US009896650B2

(12) United States Patent
Trujillo et al.

(10) Patent No.: US 9,896,650 B2
(45) Date of Patent: Feb. 20, 2018

(54) ENCAPSULATES

(71) Applicant: The Procter & Gamble Company, Cincinnati, OH (US)

(72) Inventors: Rafael Trujillo, Mason, OH (US); Johan Smets, Lubbeek (BE); An Pintens, Brasschaat (BE); Amanda Kiser Jukes, Tyne and Wear (GB); Christine Marie Cahen, Virginia Water (GB)

(73) Assignee: The Procter & Gamble Company, Cincinnati, OH (US)

( * ) Notice: Subject to any disclaimer, the term of this patent is extended or adjusted under 35 U.S.C. 154(b) by 63 days.

(21) Appl. No.: 15/189,035

(22) Filed: Jun. 22, 2016

(65) Prior Publication Data

US 2016/0369212 A1 Dec. 22, 2016

Related U.S. Application Data

(60) Provisional application No. 62/182,693, filed on Jun. 22, 2015.

(51) Int. Cl.
| | | |
|---|---|---|
| *C11D 3/50* | (2006.01) | |
| *A61K 8/11* | (2006.01) | |
| *A61Q 5/02* | (2006.01) | |
| *A61Q 13/00* | (2006.01) | |
| *C11B 9/00* | (2006.01) | |
| *C11D 17/00* | (2006.01) | |

(52) U.S. Cl.
CPC .............. *C11D 3/505* (2013.01); *A61K 8/11* (2013.01); *A61Q 5/02* (2013.01); *A61Q 13/00* (2013.01); *C11B 9/00* (2013.01); *C11B 9/003* (2013.01); *C11B 9/0007* (2013.01); *C11B 9/008* (2013.01); *C11B 9/0015* (2013.01); *C11B 9/0019* (2013.01); *C11B 9/0034* (2013.01); *C11B 9/0049* (2013.01); *C11B 9/0053* (2013.01); *C11B 9/0061* (2013.01); *C11B 9/0065* (2013.01); *C11D 3/50* (2013.01); *C11D 17/0039* (2013.01); *A61K 2800/652* (2013.01)

(58) Field of Classification Search
CPC .................. C11D 3/50; C11D 3/505
See application file for complete search history.

(56) References Cited

U.S. PATENT DOCUMENTS

| | | | | |
|---|---|---|---|---|
| 5,652,206 A | * | 7/1997 | Bacon .................... | C11D 1/62 510/101 |
| 5,879,584 A | | 3/1999 | Bianchetti et al. | |
| 6,680,289 B1 | | 1/2004 | Woo et al. | |
| 6,869,923 B1 | | 3/2005 | Cunningham et al. | |
| 7,998,403 B2 | | 8/2011 | Uchiyama et al. | |
| 2005/0276831 A1 | | 12/2005 | Dihora et al. | |
| 2007/0020263 A1 | | 1/2007 | Shitara et al. | |
| 2007/0054815 A1 | * | 3/2007 | Convents ............... | C11D 3/386 510/101 |
| 2007/0072785 A1 | * | 3/2007 | Sahin Topkara ....... | C11D 3/386 510/296 |
| 2007/0099804 A1 | * | 5/2007 | Fadel ...................... | C11D 3/50 510/101 |
| 2008/0221003 A1 | * | 9/2008 | Meine .................... | C11D 3/505 510/103 |
| 2009/0156456 A1 | | 6/2009 | Closson et al. | |
| 2011/0107524 A1 | * | 5/2011 | Chieffi .................. | A01N 25/28 8/137 |
| 2011/0305659 A1 | * | 12/2011 | Woo ........................ | A61L 9/01 424/76.21 |
| 2012/0277321 A1 | * | 11/2012 | Le-Thiesse ............. | C07C 45/81 514/770 |
| 2012/0288448 A1 | | 11/2012 | Nwachukwu et al. | |
| 2012/0322709 A1 | * | 12/2012 | Li ............................ | A61K 8/33 510/103 |
| 2013/0203863 A1 | * | 8/2013 | Le-Thiesse ........... | A23L 1/22657 514/772 |
| 2014/0315772 A1 | * | 10/2014 | Cunningham ........... | C11D 3/505 510/103 |
| 2015/0267144 A1 | * | 9/2015 | Brain ..................... | A61K 8/11 510/102 |
| 2015/0374599 A1 | * | 12/2015 | Schmaus ................ | A61K 8/35 514/772 |
| 2016/0333291 A1 | * | 11/2016 | Aida ..................... | A23L 27/204 |

OTHER PUBLICATIONS

Escher, S. D., et al., A Quantitative Study of Factors That Influence the Substantivity of Fragrance Chemicals on Laundered and Dried Fabrics, Journal of the American Oil Chemists' Society (JAOCS), Jan. 1, 1994, pp. 31-40, vol. 71, No. 1, Springer, DE, XP000420603.
International Search Report; International Application No. PCT/US2016/038617; dated Sep. 14, 2016; 13 pages.

* cited by examiner

*Primary Examiner* — John R Hardee

(74) *Attorney, Agent, or Firm* — James F. McBride; Steven W. Miller

(57) ABSTRACT

The present application relates to perfume compositions, delivery systems comprising such perfumes products comprising such perfumes and/or delivery systems, and processes for making and using same. Such perfumes and delivery systems provide improved perfume performance under high soil conditions and in cold water washing and a shell that at least partially surrounds said core.

13 Claims, No Drawings

ENCAPSULATES

FIELD OF INVENTION

The present application relates to perfume compositions, delivery systems comprising such perfumes, products comprising such perfumes and/or delivery systems, and processes for making and using same.

BACKGROUND OF THE INVENTION

Perfumes are typically individually formulated for each product that they are intended to "perfume" as perfumes tend to be product specific. This specificity is driven by the raw materials in the finished product and its intended use. As a result, the number of perfumes that a consumer products company has to formulate can be enormous. In addition, the large number of perfumes complicates the manufacturing process as they must be stored separately and each time a product switch is made, there is a significant clean-up burden on the plant as any residual perfume must be removed from the production equipment. Thus, what is needed are perfumes that can be used in multiple products. Here, the inventors have found that specific combinations of perfume raw materials (PRM's) provide a variable character that can signal different desired benefits. In short, in one type of product, for example a liquid laundry detergent, such combinations provide a character that provides an impression of enhanced cleaning while the same combination of PRMs when placed in a liquid fabric enhancer provides the impression of enhanced softness. This effect is particularly enhanced when such combinations of perfumes are encapsulated.

SUMMARY OF THE INVENTION

The present application relates to perfume compositions, delivery systems comprising such perfumes, products comprising such perfumes and/or delivery systems, and processes for making and using same.

DETAILED DESCRIPTION OF THE INVENTION

Definitions

As used herein "consumer product" means baby care, beauty care, fabric & home care, family care, feminine care, health care, or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, and feminine napkins.

As used herein, the term "cleaning and/or treatment composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof.

As used herein, the articles "a" and "an" when used in a claim, are understood to mean one or more of what is claimed or described.

As used herein, the terms "include", "includes" and "including" are meant to be synonymous with the phrase "including but not limited to".

As used herein, the term "solid" includes granular, powder, bar and tablet product forms.

As used herein, the term "situs" includes paper products, fabrics, garments, hard surfaces, hair and skin.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Perfume

The Table 1, Table 2, Table 3, Table 4 and Table 5 perfumes are disclosed. Each Table is the formula for a perfume.

TABLE 1

| No. | Common Name | CAS No. | IUPAC Name | Range 1 | Range 2 | Range 3 |
|---|---|---|---|---|---|---|
| 1 | Damascenone Total 937459 | 23696-85-7 | 1-(2,6,6-Trimethyl-1,3-cyclohexadien-1-yl)-2-butene-1-one | 0.013-0.1 | 0.03-0.07 | 0.04-0.06 |
| 2 | Neo Hivernal | 300371-33-9 | 2,3-dihydro-1,1-dimethyl-1H-Indene-ar-propanal | 0.025-0.2 | 0.070-0.135 | 0.08-0.118 |
| 3 | Neobutenone Alpha | 56973-85-4 | 1-(5,5-Dimethyl-1-cyclohexen-1-yl)-4-penten-1-one | 0.025-0.2 | 0.070-0.135 | 0.08-0.118 |
| 4 | Intreleven Aldehyde | 1337-83-3 | Undec-9-enal | 0.037-0.3 | 0.1-0.2 | 0.12-0.177 |
| 5 | Violettyne Mip (991805) | 166432-52-6 | 1,3-Undecadien-5-yne | 0.037-0.3 | 0.1-0.2 | 0.120-0.177 |
| 6 | Ebanol | 67801-20-1 | 3-Methyl-5-(2,2,3-trimethyl-3-cyclopenten-1-yl)-penten-2-ol | 0.05-0.4 | 0.13-0.27 | 0.16-0.24 |
| 7 | Para Cresyl Methyl Ether | 104-93-8 | 1-methoxy-4-methyl-benzene | 0.05-0.4 | 0.13-0.27 | 0.16-0.24 |
| 8 | Rosalva | 13019-22-2 | 9-Decen-1-ol | 0.05-0.4 | 0.13-0.27 | 0.16-0.24 |
| 9 | Methyl Nonyl Acetaldehyde | 110-41-8 | 2-methyl-undecanal | 0.06-0.5 | 0.16-0.33 | 0.2-0.3 |
| 10 | Cyclo Galbanate | 68901-15-5 | Prop-2-enyl 2-cyclohexyloxyacetate | 0.075-0.6 | 0.2-0.4 | 0.24-0.35 |
| 11 | Citronellyl Oxyacetaldehyde | 7492-67-3 | 2-[(3,7-dimethyl-6-octen-1-yl)oxy]-acetaldehyde | 0.1-0.8 | 0.27-0.54 | 0.32-0.47 |
| 12 | Methyl Iso Butenyl Tetrahydro Pyran | 16409-43-1 | Tetrahydro-4-methyl-2-(2-methyl-1-propen-1-yl)-2H-Pyran, | 0.1-0.8 | 0.27-0.54 | 0.32-0.47 |
| 13 | Eugenol | 97-53-0 | 2-Methoxy-4-(2-propen-1-yl)-phenol | 0.110-0.9 | 0.3-0.6 | 0.36-0.53 |
| 14 | Ethyl Oenanthate | 106-30-9 | Heptanoic acid, ethyl ester | 0.125-1 | 0.335-0.675 | 0.4-0.6 |
| 15 | Geranyl Acetate | 105-87-3 | (2E)-3,7-Dimethyl-2,6-Octadien-1-ol-1-acetate | 0.125-1 | 0.335-0.675 | 0.4-0.6 |
| 16 | Melonal | 106-72-9 | 2,6-Dimethyl-5-heptenal | 0.125-1 | 0.335-0.675 | 0.4-0.6 |
| 17 | Methyl Benzoate | 93-58-3 | Methyl benzoate | 0.125-1 | 0.335-0.675 | 0.4-0.6 |
| 18 | Dimethyl Benzyl Carbinyl Acetate | 151-05-3 | (2-methyl-1-phenylpropan-2-yl) acetate | 0.150-1.2 | 0.402-0.8 | 0.48-0.7 |
| 19 | Eucalyptol | 470-82-6 | 1,3,3-Trimethyl-2-oxabicyclo[2.2.2]octane | 0.150-1.2 | 0.402-0.8 | 0.48-0.7 |
| 20 | Floriane | 1447721-00-7 | 2,6-dimethyl-3a-(1-methylethyl)-octahydro benzofuran | 0.175-1.4 | 0.47-0.9 | 0.56-0.82 |
| 21 | Undecavertol | 81782-77-6 | 4-Methyl-3-decen-5-ol | 0.180-1.5 | 0.5-1 | 0.6-0.82 |
| 22 | Lime Oxide | 73018-51-6 | 1,6-Octadien-3-ol, 3,7-dimethyl-, acid-isomerized | 0.2-1.6 | 0.536-1.08 | 0.64-0.94 |
| 23 | Allyl Cyclohexane Propionate | 2705-87-5 | Prop-2-enyl 3-cyclohexylpropanoate | 0.25-2 | 0.67 1.35 | 0.8-1.2 |
| 24 | Anisic Aldehyde | 123-11-5 | 4-Methoxy-benzaldehyde | 0.25-2 | 0.67 1.35 | 0.8-1.2 |
| 25 | Beta Naphthol Methyl Ether | 93-04-9 | 2-Methoxy-naphthalene | 0.25-2 | 0.67 1.35 | 0.8-1.2 |
| 26 | Citronellal | 106-23-0 | 3,7-Dimethyl-6-octenal | 0.25-2 | | 0.8-1.2 |
| 27 | Florhydral | 125109-85-5 | β-Methyl-3-(1-methylethyl)-benzenepropanal | 0.25-2 | 0.67 1.35 | 0.8-1.2 |
| 28 | Ligustral Or Triplal | 68039-49-6 | 2,4-Dimethyl-3-Cyclohexene-1-carboxaldehyde | 0.25-2 | 0.67 1.35 | 0.8-1.2 |
| 29 | Pinyl Isobutyrald Alpha | 33885-52-8 | α,α,6,6-tetramethyl-bicyclo[3.1.1]hept-2-ene-2-propanal | 0.25-2 | 0.67 1.35 | 0.8-1.2 |
| 30 | Prenyl Acetate | 1191-16-8 | 2-Buten-1-ol, 3-methyl 1-acetate | 0.25-2 | 0.67 1.35 | 0.8-1.2 |
| 31 | Delta Damascone | 57378-68-4 | 1-(2,6,6-trimethyl-3-cyclohexen-1-yl)-2-buten-1-one | 0.375-3 | 1-2 | 1.2-1.8 |

TABLE 1-continued

| No. | Common Name | CAS No. | IUPAC Name | Range 1 | Range 2 | Range 3 |
|---|---|---|---|---|---|---|
| 32 | Linalyl Acetate | 115-95-7 | 3,7-Dimethyl-1,6-octadien-3-acetate | 0.5-4 | 1.34-2.7 | 1.6-2.4 |
| 33 | 4-Tertiary Butyl Cyclohexyl Acetate | 32210-23-4 | 4-(1,1-dimethylethyl)-cyclohexanol-1-acetate | 1-8 | 2.68-5.4 | 3.2-4.72 |
| 34 | Amyl Salicylate | 2050-08-0 | 2-Hydroxybenzoic acid pentyl ester | 1-8 | 2.68-5.4 | 3.2-4.72 |
| 35 | Cyclohexyl Salicylate | 25485-88-5 | 2-hydroxy-benzoic acid-cyclohexyl ester | 1-8 | 2.68-5.4 | 3.2-4.72 |
| 36 | Dihydro Myrcenol | 18479-58-8 | 2,6-Dimethyl-7-octen-2-ol, | | | |
| 37 | Iso E Super Or Wood | 54464-57-2 | 1-(1,2,3,4,5,6,7,8-octahydro-2,3,8,8-tetramethyl-2-naphthalenyl)-ethanone | 1-8 | 2.68-5.4 | 3.2-4.72 |
| 38 | Neobergamate Forte (Q) | 69103-01-1 | (2-methyl-6-methylideneoct-7-en-2-yl) acetate | 1-8 | 2.68-5.4 | 3.2-4.72 |
| 39 | Terpinyl Acetate | 80-26-2 | 2-(4-methyl-1-cyclohex-3-enyl)propan-2-yl acetate | 1-8 | 2.68-5.4 | 3.2-4.72 |
| 40 | Citronellyl Nitrile | 51566-62-2 | 3,7-dimethyl-6-Octenenitrile | 1.25-10 | 3.35-6.75 | 4-5.9 |
| 41 | Hexyl Salicylate | 6259-76-3 | Hexyl 2-hydroxybenzoate | 1.25-10 | 3.35-6.75 | 4-5.9 |
| 42 | Orange Terpenes | 8028-48-6 | Unspecified | 1.25-10 | 3.35-6.75 | 4-5.9 |
| 43 | Flor Acetate | 54830-99-8 | 3a,4,5,6,7,7a-hexahydro-4,7-Methano-1H-indenol acetate Incompletely Defined Substance | 1.75-14 | 4.7-9.45 | 5.6-8.26 |
| 44 | Frutene | 68912-13-0 | 4,7-Methano-1H-indenol, 3a,4,5,6,7,7a-hexahydro-, propanoate Incompletely Defined Substance | 2.2-17.5 | 6-11.9 | 7.04-10.4 |
| 45 | Koavone | 81786-73-4 | (3Z)-3,4,5,6,6-Pentamethyl-3-hepten-2-one | 2.2-17.5 | 6-12.5 | 7.4-11 |
| 46 | Verdox | 88-41-5 | 2-(1,1-Dimethylethyl)cyclohexyl acetate | 3-24 | 8-16.2 | 9.6-14.2 |

TABLE 2

| No. | Common Name | CAS No. | IPUAC Name | Range 1 | Range 2 | Range 3 |
|---|---|---|---|---|---|---|
| 1 | Cis-6-Nonen-1-OL FCC | 35854-86-5 | (Z)-non-6-en-1-ol | 0.0167-0.15 | 0.025-0.075 | 0.03-0.06 |
| 2 | Javanol (Conf.-Giv) | 198404-98-7 | 1-methyl-2-[(1,2,2-trimethylbicyclo[3.1.0]hex-3-yl)methyl]-cyclopropanemethanol | 0.02-0.18 | 0.03-0.09 | 0.05-0.07 |
| 3 | E Z-2,6-Nonadien-1-al FCC | 557-48-2 | (2E,6Z)-nona-2,6-dienal | 0.003-0.03 | 0.005-0.015 | 0.005-0.015 |
| 4 | Ethyl Vanillin | 121-32-4 | 3-Ethoxy-4-hydroxy-benzaldehyde | 0.03-0.3 | 0.050-0.15 | 0.08-0.12 |
| 5 | Helvetolide 947650 | 141773-73-1 | [2-[1-(3,3-dimethylcyclohexyl)ethoxy]-2-methylpropyl]propanoate | 0.05-0.45 | 0.075-0.225 | 0.12-0.18 |
| 6 | Lime Oxide | 73018-51-6 | Unspecified 1,6-Octadien-3-ol, 3,7-dimethyl-, acid-isomerized | 0.06-0.6 | 0.1-0.3 | 0.15-0.25 |

TABLE 2-continued

| No. | Common Name | CAS No. | IPUAC Name | Range 1 | Range 2 | Range 3 |
|---|---|---|---|---|---|---|
| 7 | Violiff | 87731-18-8 | [(4Z)-1-Cyclooct-4-enyl] methyl carbonate | 0.06-0.6 | 0.1-0.3 | 0.15-0.25 |
| 8 | Dupical | 30168-23-1 | 4-(Octahydro-4,7-methano-5H-inden-5-ylidene)butanal | 0.06-0.6 | 0.1-0.3 | 0.15-0.25 |
| 9 | Nirvanol 974650 | 107898-54-4 | 3,3-Dimethyl-5-(2,2,3-trimethyl-3-cyclopenten-1-yl)-4-penten-2-ol | 0.1-0.9 | 0.15-0.45 | 0.24-0.36 |
| 10 | Neobutenone Alpha | 56973-85-4 | 1-(5,5-Dimethyl-1-cyclohexen-1-yl)-4-penten-1-one | 0.115-1 | 0.175-0.525 | 0.27-0.45 |
| 11 | Habanolide 100% | 111879-80-2 | (12E)--oxacyclohexadec-12-en-2-one | 0.115-1 | 0.175-0.525 | 0.28-0.45 |
| 12 | Decyl Aldehyde | 112-31-2 | Decanal | 0.115-1 | 0.175-0.6 | 0.28-0.45 |
| 13 | Lauric Aldehyde | 112-54-9 | Dodecanal | 0.166-1.5 | 0.25-0.75 | 0.4-0.6 |
| 14 | Diphenyl Oxide | 101-84-8 | 1,1'-oxybis-benzene | 0.2-1.8 | 0.3-0.9 | 0.48-0.72 |
| 15 | Melonal | 106-72-9 | 2,6-dimethyl-5-Heptenal | 0.23-2.1 | 0.35-1.05 | 0.56-0.85 |
| 16 | Florhydral | 125109-85-5 | β-Methyl-3-(1-methylethyl)-benzenepropanal | 0.33-3 | 0.5-1.5 | 0.8-1.2 |
| 17 | Allyl Cyclohexane Propionate | 2705-87-5 | Prop-2-enyl 3-cyclohexylpropanoate | 0.7-6.6 | 1.1-3.3 | 1.76-2.64 |
| 18 | Floralozone | 67634-15-5 | 4-EThyl-α,α-dimethyl-benzenepropanal | 0.67-6 | 1-3 | 1.6-2.4 |
| 19 | Methyl Phenyl Carbinyl Acetate | 93-92-5 | 1-phenylethyl acetate | 0.8-7.2 | 1.2-4 | 1.9-2.9 |
| 20 | Pinyl Isobutyrald Alpha | 33885-52-8 | α,α,6,6-tetramethyl-bicyclo[3.1.1]hept-2-ene-2-propanal | 0.8-7.5 | 1.25-4 | 2-3 |
| 21 | FRUCTALATE 943871 | 72903-27-6 | Diethyl cyclohexane-1,4-dicarboxylate | 1-9 | 1.5-4.5 | 2.4-3.6 |
| 22 | Ligustral Or Triplal | 68039-49-6 | 2,4-Dimethyl-3-Cyclohexene-1-carboxaldehyde | 1.17-10.5 | 1.75-5 | 2.8-4.2 |
| 23 | Koavone | 81786-73-4 | (3Z)-3,4,5,6,6-pentamethyl-3-Hepten-2-one | 1.3-12 | 2-6 | 3.2-4.8 |
| 24 | Nectaryl | 95962-14-4 | 2-[2-(4-methyl-3-cyclohexen-1-yl)propyl] cyclopentanone | 1.3-12 | 2-6 | 3.2-4.8 |
| 25 | Jasmal | 18871-14-2 | (3-pentyloxan-4-yl) acetate | 1.3-12 | 2-6 | 3.2-4.8 |
| 26 | Ionone Beta | 14901-07-6 | 4-(2,6,6-Trimethyl-1-cyclohexen-1-yl)-3-buten-2-one | 1.5-13.5 | 2.25-6 | 3.6-5.4 |
| 27 | Methyl Dihydro Jasmonate | 24851-98-7 | 3-oxo-2-pentyl-cyclopentaneacetic acid methyl ester | 1.5-13.5 | 2.25-6 | 3.6-5.4 |
| 28 | 4-Tertiary Butyl Cyclohexyl Acetate | 32210-23-4 | 4-(1,1-Dimethylethyl)cyclohexyl acetate | 1.66-15 | 2.5-7.5 | 4-6 |
| 29 | Ethyl-2-Methyl Butyrate | 7452-79-1 | Ethyl 2-methylbutanoate | 1.66-15 | 2.5-7.5 | 4-6 |
| 30 | Orange Terpenes | 8028-48-6 | Unspecified | 2-18 | 3-9 | 4.8-7.5 |
| 31 | Dihydro Myrcenol | 18479-58-8 | 2,6-Dimethyl-7-octen-2-ol | 2.16-20 | 3-9 | 5.2-7.8 |
| 32 | Tetra Hydro Linalool | 78-69-3 | 3,7-dimethyl-3-octanol | 3.5-30 | 5-16 | 8-12 |

TABLE 2-continued

| No. | Common Name | CAS No. | IPUAC Name | Range 1 | Range 2 | Range 3 |
|---|---|---|---|---|---|---|
| 33 | Verdox | 88-41-5 | (2-tert-butylcyclohexyl) acetate | 3-25 | 4-14 | 7.5-11 |
| 34 | Flor Acetate | 5413-60-5 | 3a,4,5,6,7,7a-hexahydro-4,7-methano-1H-inden-6-yl acetate | 5-40 | 8-25 | 14-17 |

TABLE 3

| No. | Common Name | CAS No. | IUPAC Name | Range 1 | Range 2 | Range 3 |
|---|---|---|---|---|---|---|
| 1 | Damascenone Total 937459 | 23696-85-7 | 1-(2,6,6-Trimethyl-1,3-cyclohexadien-1-yl)-2-butene-1-one | 0.013-0.1 | 0.03-0.07 | 0.04-0.06 |
| 2 | Neo Hivernal | 300371-33-9 | 2,3-dihydro-1,1-dimethyl-1H-Indene-ar-propanal | 0.025-0.2 | 0.070-0.135 | 0.08-0.118 |
| 3 | Neobutenone Alpha | 56973-85-4 | 1-(5,5-Dimethyl-1-cyclohexen-1-yl)-4-penten-1-one | 0.025-0.2 | 0.070-0.135 | 0.08-0.118 |
| 4 | Intreleven Aldehyde | 1337-83-3 | Undec-9-enal | 0.037-0.3 | 0.1-0.2 | 0.12-0.177 |
| 5 | Violettyne Mip (991805) | 166432-52-6 | 1,3-Undecadien-5-yne | 0.037-0.3 | 0.1-0.2 | 0.120-0.177 |
| 6 | Ebanol | 67801-20-1 | 3-Methyl-5-(2,2,3-trimethyl-3-cyclopenten-1-yl)-penten-2-ol | 0.05-0.4 | 0.13-0.27 | 0.16-0.24 |
| 7 | Para Cresyl Methyl Ether | 104-93-8 | 1-methoxy-4-methyl-benzene | 0.05-0.4 | 0.13-0.27 | 0.16-0.24 |
| 8 | Rosalva | 13019-22-2 | 9-Decen-1-ol | 0.05-0.4 | 0.13-0.27 | 0.16-0.24 |
| 9 | Methyl Nonyl Acetaldehyde | 110-41-8 | 2-methyl-undecanal | 0.06-0.5 | 0.16-0.33 | 0.2-0.3 |
| 10 | Cyclo Galbanate | 68901-15-5 | Prop-2-enyl 2-cyclohexyloxyacetate | 0.075-0.6 | 0.2-0.4 | 0.24-0.35 |
| 11 | Citronellyl Oxyacetaldehyde | 7492-67-3 | 2-[(3,7-dimethyl-6-octen-1-yl)oxy]-acetaldehyde | 0.1-0.8 | 0.27-0.54 | 0.32-0.47 |
| 12 | Methyl Iso Butenyl Tetrahydro Pyran | 16409-43-1 | Tetrahydro-4-methyl-2-(2-methyl-1-propen-1-yl)-2H-Pyran, | 0.1-0.8 | 0.27-0.54 | 0.32-0.47 |
| 13 | Eugenol | 97-53-0 | 2-Methoxy-4-(2-propen-1-yl)-phenol | 0.110-0.9 | 0.3-0.6 | 0.36-0.53 |
| 14 | Ethyl Oenanthate | 106-30-9 | Heptanoic acid, ethyl ester | 0.125-1 | 0.335-0.675 | 0.4-0.6 |
| 15 | Geranyl Acetate | 105-87-3 | (2E)-3,7-Dimethyl-2,6-Octadien-1-ol-1-acetate | 0.125-1 | 0.335-0.675 | 0.4-0.6 |
| 16 | Melonal | 106-72-9 | 2,6-Dimethyl-5-heptenal | 0.125-1 | 0.335-0.675 | 0.4-0.6 |
| 17 | Methyl Benzoate | 93-58-3 | Methyl benzoate | 0.125-1 | 0.335-0.675 | 0.4-0.6 |
| 18 | Dimethyl Benzyl Carbinyl Acetate | 151-05-3 | (2-methyl-1-phenylpropan-2-yl) acetate | 0.150-1.2 | 0.402-0.8 | 0.48-0.7 |
| 19 | Eucalyptol | 470-82-6 | 1,3,3-Trimethyl-2-oxabicyclo[2.2.2]octane | 0.150-1.2 | 0.402-0.8 | 0.48-0.7 |
| 20 | Floriane | 1447721-00-7 | 2,6-dimethyl-3a-(1-methylethyl)-octahydro benzofuran | 0.175-1.4 | 0.47-0.9 | 0.56-0.82 |
| 21 | Undecavertol | 81782-77-6 | 4-Methyl-3-decen-5-ol | 0.180-1.5 | 0.5-1 | 0.6-0.82 |
| 22 | Lime Oxide | 73018-51-6 | 1,6-Octadien-3-ol, 3,7-dimethyl-, acid-isomerized | 0.2-1.6 | 0.536-1.08 | 0.64-0.94 |
| 23 | Allyl Cyclohexane Propionate | 2705-87-5 | Prop-2-enyl 3-cyclohexylpropanoate | 0.25-2 | 0.67 1.35 | 0.8-1.2 |
| 24 | Anisic Aldehyde | 123-11-5 | 4-Methoxy-benzaldehyde | 0.25-2 | 0.67 1.35 | 0.8-1.2 |
| 25 | Beta Naphthol Methyl Ether | 93-04-9 | 2-Methoxy-naphthalene | 0.25-2 | 0.67 1.35 | 0.8-1.2 |

TABLE 3-continued

| No. | Common Name | CAS No. | IUPAC Name | Range 1 | Range 2 | Range 3 |
|---|---|---|---|---|---|---|
| 26 | Citronellal | 106-23-0 | 3,7-Dimethyl-6-octenal | 0.25-2 | 0.05-1.6 | 0.8-1.2 |
| 27 | Florhydral | 125109-85-5 | β-Methyl-3-(1-methylethyl)-benzenepropanal | 0.25-2 | 0.67 1.35 | 0.8-1.2 |
| 28 | Ligustral Or Triplal | 68039-49-6 | 2,4-Dimethyl-3-Cyclohexene-1-carboxaldehyde | 0.25-2 | 0.67 1.35 | 0.8-1.2 |
| 29 | Pinyl Isobutyrald Alpha | 33885-52-8 | α,α,6,6-tetramethyl-bicyclo[3.1.1]hept-2-ene-2-propanal | 0.25-2 | 0.67 1.35 | 0.8-1.2 |
| 30 | Prenyl Acetate | 1191-16-8 | 2-Buten-1-ol, 3-methyl 1-acetate | 0.25-2 | 0.67 1.35 | 0.8-1.2 |
| 31 | Delta Damascone | 57378-68-4 | 1-(2,6,6-trimethyl-3-cyclohexen-1-yl)-2-buten-1-one | 0.375-3 | 1-2 | 1.2-1.8 |
| 32 | Linalyl Acetate | 115-95-7 | 3,7-Dimethyl-1,6-octadien-3-acetate | 0.5-4 | 1.34-2.7 | 1.6-2.4 |
| 33 | 4-Tertiary Butyl Cyclohexyl Acetate | 32210-23-4 | 4-(1,1-dimethylethyl)-cyclohexanol-1-acetate | 1-8 | 2.68-5.4 | 3.2-4.72 |
| 34 | Amyl Salicylate | 2050-08-0 | 2-Hydroxybenzoic acid pentyl ester | 1-8 | 2.68-5.4 | 3.2-4.72 |
| 35 | Cyclohexyl Salicylate | 25485-88-5 | 2-hydroxy-benzoic acid-cyclohexyl ester | 1-8 | 2.68-5.4 | 3.2-4.72 |
| 36 | Dihydro Myrcenol | 18479-58-8 | 2,6-Dimethyl-7-octen-2-ol, | 1-7 | 2.5-5.5 | 3.5-4.5 |
| 37 | Iso E Super Or Wood | 54464-57-2 | 1-(1,2,3,4,5,6,7,8-octahydro-2,3,8,8-tetramethyl-2-naphthalenyl)-ethanone | 1-8 | 2.68-5.4 | 3.2-4.72 |
| 38 | Neobergamate Forte (Q) | 69103-01-1 | (2-methyl-6-methylideneoct-7-en-2-yl) acetate | 1-8 | 2.68-5.4 | 3.2-4.72 |
| 39 | Terpinyl Acetate | 80-26-2 | 2-(4-methyl-1-cyclohex-3-enyl)propan-2-yl acetate | 1-8 | 2.68-5.4 | 3.2-4.72 |
| 40 | Citronellyl Nitrile | 51566-62-2 | 3,7-dimethyl-6-Octenenitrile | 1.25-10 | 3.35-6.75 | 4-5.9 |
| 41 | Hexyl Salicylate | 6259-76-3 | Hexyl 2-hydroxybenzoate | 1.25-10 | 3.35-6.75 | 4-5.9 |
| 42 | Orange Terpenes | 8028-48-6 | Unspecified | 1.25-10 | 3.35-6.75 | 4-5.9 |
| 43 | Flor Acetate | 54830-99-8 | 3a,4,5,6,7,7a-hexahydro-4,7-Methano-1H-indenol acetate Incompletely Defined Substance | 1.75-14 | 4.7-9.45 | 5.6-8.26 |
| 44 | Frutene | 68912-13-0 | 4,7-Methano-1H-indenol, 3a,4,5,6,7,7a-hexahydro-, propanoate Incompletely Defined Substance | 2.2-17.5 | 6-11.9 | 7.04-10.4 |
| 45 | Koavone | 81786-73-4 | (3Z)-3,4,5,6,6-Pentamethyl-3-hepten-2-one | 2.2-17.5 | 6-12.5 | 7.4-11 |
| 46 | Verdox | 88-41-5 | 2-(1,1-Dimethylethyl)cyclohexyl acetate | 3-24 | 8-16.2 | 9.6-14.2 |

TABLE 4

| No. | Common Name | CAS No. | IUPAC Name | Range 1 | Range 2 | Range 3 |
|---|---|---|---|---|---|---|
| 1 | Damascenone Total 937459 | 23696-85-7 | 1-(2,6,6-Trimethyl-1,3-cyclohexadien-1-yl)-2-butene-1-one | 0.013-0.1 | 0.03-0.07 | 0.04-0.06 |
| 2 | Neo Hivernal | 300371-33-9 | 2,3-dihydro-1,1-dimethyl-1H-Indene-ar-propanal | 0.025-0.2 | 0.070-0.135 | 0.08-0.118 |

TABLE 4-continued

| No. | Common Name | CAS No. | IUPAC Name | Range 1 | Range 2 | Range 3 |
|---|---|---|---|---|---|---|
| 3 | Neobutenone Alpha | 56973-85-4 | 1-(5,5-Dimethyl-1-cyclohexen-1-yl)-4-penten-1-one | 0.025-0.2 | 0.070-0.135 | 0.08-0.118 |
| 4 | Intreleven Aldehyde | 1337-83-3 | Undec-9-enal | 0.037-0.3 | 0.1-0.2 | 0.12-0.177 |
| 5 | Violettyne Mip (991805) | 166432-52-6 | 1,3-Undecadien-5-yne | 0.037-0.3 | 0.1-0.2 | 0.120-0.177 |
| 6 | Para Cresyl Methyl Ether | 104-93-8 | 1-methoxy-4-methyl-benzene | 0.05-0.4 | 0.13-0.27 | 0.16-0.24 |
| 7 | Rosalva | 13019-22-2 | 9-Decen-1-ol | 0.05-0.4 | 0.13-0.27 | 0.16-0.24 |
| 8 | Methyl Nonyl Acetaldehyde | 110-41-8 | 2-methyl-undecanal | 0.06-0.5 | 0.16-0.33 | 0.2-0.3 |
| 9 | Cyclo Galbanate | 68901-15-5 | Prop-2-enyl 2-cyclohexyloxyacetate | 0.075-0.6 | 0.2-0.4 | 0.24-0.35 |
| 10 | Citronellyl Oxyacetaldehyde | 7492-67-3 | 2-[(3,7-dimethyl-6-octen-1-yl)oxy]-acetaldehyde | 0.1-0.8 | 0.27-0.54 | 0.32-0.47 |
| 11 | Methyl Iso Butenyl Tetrahydro Pyran | 16409-43-1 | Tetrahydro-4-methyl-2-(2-methyl-1-propen-1-yl)-2H-Pyran, | 0.1-0.8 | 0.27-0.54 | 0.32-0.47 |
| 12 | Eugenol | 97-53-0 | 2-Methoxy-4-(2-propen-1-yl)-phenol | 0.110-0.9 | 0.3-0.6 | 0.36-0.53 |
| 13 | Ethyl Oenanthate | 106-30-9 | Heptanoic acid, ethyl ester | 0.125-1 | 0.335-0.675 | 0.4-0.6 |
| 14 | Geranyl Acetate | 105-87-3 | (2E)-3,7-Dimethyl-2,6-Octadien-1-ol-1-acetate | 0.125-1 | 0.335-0.675 | 0.4-0.6 |
| 15 | Melonal | 106-72-9 | 2,6-Dimethyl-5-heptenal | 0.125-1 | 0.335-0.675 | 0.4-0.6 |
| 16 | Methyl Benzoate | 93-58-3 | Methyl benzoate | 0.125-1 | 0.335-0.675 | 0.4-0.6 |
| 17 | Dimethyl Benzyl Carbinyl Acetate | 151-05-3 | (2-methyl-1-phenylpropan-2-yl) acetate | 0.150-1.2 | 0.402-0.8 | 0.48-0.7 |
| 18 | Eucalyptol | 470-82-6 | 1,3,3-Trimethyl-2-oxabicyclo[2.2.2]octane | 0.150-1.2 | 0.402-0.8 | 0.48-0.7 |
| 19 | Floriane | 1447721-00-7 | 2,6-dimethyl-3a-(1-methylethyl)-octahydro benzofuran | 0.175-1.4 | 0.47-0.9 | 0.56-0.82 |
| 20 | Undecavertol | 81782-77-6 | 4-Methyl-3-decen-5-ol | 0.180-1.5 | 0.5-1 | 0.6-0.82 |
| 21 | Lime Oxide | 73018-51-6 | 1,6-Octadien-3-ol, 3,7-dimethyl-, acid-isomerized | 0.2-1.6 | 0.536-1.08 | 0.64-0.94 |
| 22 | Allyl Cyclohexane Propionate | 2705-87-5 | Prop-2-enyl 3-cyclohexylpropanoate | 0.25-2 | 0.67 1.35 | 0.8-1.2 |
| 23 | Anisic Aldehyde | 123-11-5 | 4-Methoxy-benzaldehyde | 0.25-2 | 0.67 1.35 | 0.8-1.2 |
| 24 | Beta Naphthol Methyl Ether | 93-04-9 | 2-Methoxy-naphthalene | 0.25-2 | 0.67 1.35 | 0.8-1.2 |
| 25 | Citronellal | 106-23-0 | 3,7-Dimethyl-6-octenal | 0.25-2 | 0.05-1.6 | 0.8-1.2 |
| 26 | Florhydral | 125109-85-5 | β-Methyl-3-(1-methylethyl)-benzenepropanal | 0.25-2 | 0.67 1.35 | 0.8-1.2 |
| 27 | Ligustral Or Triplal | 68039-49-6 | 2,4-Dimethyl-3-Cyclohexene-1-carboxaldehyde | 0.25-2 | 0.67 1.35 | 0.8-1.2 |
| 28 | Pinyl Isobutyrald Alpha | 33885-52-8 | α,α,6,6-tetramethyl-bicyclo[3.1.1]hept-2-ene-2-propanal | 0.25-2 | 0.67 1.35 | 0.8-1.2 |
| 29 | Prenyl Acetate | 1191-16-8 | 2-Buten-1-ol, 3-methyl 1-acetate | 0.25-2 | 0.67 1.35 | 0.8-1.2 |
| 30 | Delta Damascone | 57378-68-4 | 1-(2,6,6-trimethyl-3-cyclohexen-1-yl)-2-buten-1-one | 0.375-3 | 1-2 | 1.2-1.8 |
| 31 | Linalyl Acetate | 115-95-7 | 3,7-Dimethyl-1,6-octadien-3-acetate | 0.5-4 | 1.34-2.7 | 1.6-2.4 |
| 32 | 4-Tertiary Butyl Cyclohexyl Acetate | 32210-23-4 | 4-(1,1-dimethylethyl)-cyclohexanol-1-acetate | 1-8 | 2.68-5.4 | 3.2-4.72 |
| 33 | Amyl Salicylate | 2050-08-0 | 2-Hydroxybenzoic acid pentyl ester | 1-8 | 2.68-5.4 | 3.2-4.72 |
| 34 | Cyclohexyl Salicylate | 25485-88-5 | 2-hydroxy-benzoic acid-cyclohexyl ester | 1-8 | 2.68-5.4 | 3.2-4.72 |

TABLE 4-continued

| No. | Common Name | CAS No. | IUPAC Name | Range 1 | Range 2 | Range 3 |
|---|---|---|---|---|---|---|
| 35 | Dihydro Myrcenol | 18479-58-8 | 2,6-Dimethyl-7-octen-2-ol, | 1-7 | 2.5-5.5 | 3.5-4.5 |
| 36 | Iso E Super Or Wood | 54464-57-2 | 1-(1,2,3,4,5,6,7,8-octahydro-2,3,8,8-tetramethyl-2-naphthalenyl)-ethanone | 1-8 | 2.68-5.4 | 3.2-4.72 |
| 37 | Neobergamate Forte (Q) | 69103-01-1 | (2-methyl-6-methylideneoct-7-en-2-yl) acetate | 1-8 | 2.68-5.4 | 3.2-4.72 |
| 38 | Terpinyl Acetate | 80-26-2 | 2-(4-methyl-1-cyclohex-3-enyl)propan-2-yl acetate | 1-8 | 2.68-5.4 | 3.2-4.72 |
| 39 | Citronellyl Nitrile | 51566-62-2 | 3,7-dimethyl-6-Octenenitrile | 1.25-10 | 3.35-6.75 | 4-5.9 |
| 40 | Hexyl Salicylate | 6259-76-3 | Hexyl 2-hydroxybenzoate | 1.25-10 | 3.35-6.75 | 4-5.9 |
| 41 | Orange Terpenes | 8028-48-6 | Unspecified | 1.25-10 | 3.35-6.75 | 4-5.9 |
| 42 | Flor Acetate | 54830-99-8 | 3a,4,5,6,7,7a-hexahydro-4,7-Methano-1H-indenol acetate Incompletely Defined Substance | 1.75-14 | 4.7-9.45 | 5.6-8.26 |
| 43 | Frutene | 68912-13-0 | 4,7-Methano-1H-indenol, 3a,4,5,6,7,7a-hexahydro-, propanoate Incompletely Defined Substance | 2.2-17.5 | 6-11.9 | 7.04-10.4 |
| 44 | Koavone | 81786-73-4 | (3Z)-3,4,5,6,6-Pentamethyl-3-hepten-2-one | 2.2-17.5 | 6-12.5 | 7.4-11 |
| 45 | Verdox | 88-41-5 | 2-(1,1-Dimethylethyl)cyclohexyl acetate | 3-24 | 8-16.2 | 9.6-14.2 |
| 46 | Laevo trisandol | 28219-61-6 | Ethyl trimethyl cyclopentene butenol | 0.1-7 | 0.25-5 | 0.5-3 |

TABLE 5

| No. | Common Name | CAS No. | IPUAC Name | Range 1 | Range 2 | Range 3 |
|---|---|---|---|---|---|---|
| 1 | Cis-6-Nonen-1-OL FCC | 35854-86-5 | (Z)-non-6-en-1-ol | 0.0167-0.15 | 0.025-0.075 | 0.03-0.06 |
| 2 | E Z-2,6-Nonadien-1-al FCC | 557-48-2 | (2E,6Z)-nona-2,6-dienal | 0.003-0.03 | 0.005-0.015 | 0.005-0.015 |
| 3 | Ethyl Vanillin | 121-32-4 | 3-Ethoxy-4-hydroxy-benzaldehyde | 0.03-0.3 | 0.050-0.15 | 0.08-0.12 |
| 4 | Helvetolide 947650 | 141773-73-1 | [2-[1-(3,3-dimethylcyclohexyl)ethoxy]-2-methylpropyl]propanoate | 0.05-0.45 | 0.075-0.225 | 0.12-0.18 |
| 5 | Lime Oxide | 73018-51-6 | Unspecified 1,6-Octadien-3-ol, 3,7-dimethyl-, acid-isomerized | 0.06-0.6 | 0.1-0.3 | 0.15-0.25 |
| 6 | Violiff | 87731-18-8 | [(4Z)-1-Cyclooct-4-enyl] methyl carbonate | 0.06-0.6 | 0.1-0.3 | 0.15-0.25 |
| 7 | Dupical | 30168-23-1 | 4-(Octahydro-4,7-methano-5H-inden-5-ylidene)butanal | 0.06-0.6 | 0.1-0.3 | 0.15-0.25 |
| 8 | Neobutenone Alpha | 56973-85-4 | 1-(5,5-Dimethyl-1-cyclohexen-1-yl)-4-penten-1-one | 0.115-1 | 0.175-0.525 | 0.27-0.45 |
| 9 | Habanolide 100% | 111879-80-2 | (12E)--oxacyclohexadec-12-en-2-one | 0.115-1 | 0.175-0.525 | 0.28-0.45 |

TABLE 5-continued

| No. | Common Name | CAS No. | IPUAC Name | Range 1 | Range 2 | Range 3 |
|---|---|---|---|---|---|---|
| 10 | Decyl Aldehyde | 112-31-2 | Decanal | 0.115-1 | 0.175-0.6 | 0.28-0.45 |
| 11 | Lauric Aldehyde | 112-54-9 | Dodecanal | 0.166-1.5 | 0.25-0.75 | 0.4-0.6 |
| 12 | Diphenyl Oxide | 101-84-8 | 1,1'-oxybis-benzene | 0.2-1.8 | 0.3-0.9 | 0.48-0.72 |
| 13 | Melonal | 106-72-9 | 2,6-dimethyl-5-Heptenal | 0.23-2.1 | 0.35-1.05 | 0.56-0.85 |
| 14 | Florhydral | 125109-85-5 | β-Methyl-3-(1-methylethyl)-benzenepropanal | 0.33-3 | 0.5-1.5 | 0.8-1.2 |
| 15 | Allyl Cyclohexane Propionate | 2705-87-5 | Prop-2-enyl 3-cyclohexylpropanoate | 0.7-6.6 | 1.1-3.3 | 1.76-2.64 |
| 16 | Floralozone | 67634-15-5 | 4-EThyl-α,α-dimethyl-benzenepropanal | 0.67-6 | 1-3 | 1.6-2.4 |
| 17 | Methyl Phenyl Carbinyl Acetate | 93-92-5 | 1-phenylethyl acetate | 0.8-7.2 | 1.2-4 | 1.9-2.9 |
| 18 | Pinyl Isobutyrald Alpha | 33885-52-8 | α,α,6,6-tetramethyl-bicyclo[3.1.1]hept-2-ene-2-propanal | 0.8-7.5 | 1.25-4 | 2-3 |
| 19 | FRUCTALATE 943871 | 72903-27-6 | Diethyl cyclohexane-1,4-dicarboxylate | 1-9 | 1.5-4.5 | 2.4-3.6 |
| 20 | Ligustral Or Triplal | 68039-49-6 | 2,4-Dimethyl-3-Cyclohexene-1-carboxaldehyde | 1.17-10.5 | 1.75-5 | 2.8-4.2 |
| 21 | Koavone | 81786-73-4 | (3Z)-3,4,5,6,6-pentamethyl-3-Hepten-2-one | 1.3-12 | 2-6 | 3.2-4.8 |
| 22 | Nectaryl | 95962-14-4 | 2-[2-(4-methyl-3-cyclohexen-1-yl)propyl]cyclopentanone | 1.3-12 | 2-6 | 3.2-4.8 |
| 23 | Jasmal | 18871-14-2 | (3-pentyloxan-4-yl) acetate | 1.3-12 | 2-6 | 3.2-4.8 |
| 24 | Ionone Beta | 14901-07-6 | 4-(2,6,6-Trimethyl-1-cyclohexen-1-yl)-3-buten-2-one | 1.5-13.5 | 2.25-6 | 3.6-5.4 |
| 25 | Methyl Dihydro Jasmonate | 24851-98-7 | 3-oxo-2-pentyl-cyclopentaneacetic acid methyl ester | 1.5-13.5 | 2.25-6 | 3.6-5.4 |
| 26 | 4-Tertiary Butyl Cyclohexyl Acetate | 32210-23-4 | 4-(1,1-Dimethylethyl)cyclohexyl acetate | 1.66-15 | 2.5-7.5 | 4-6 |
| 27 | Ethyl-2-Methyl Butyrate | 7452-79-1 | Ethyl 2-methylbutanoate | 1.66-15 | 2.5-7.5 | 4-6 |
| 28 | Orange Terpenes | 8028-48-6 | Unspecified | 2-18 | 3-9 | 4.8-7.5 |
| 29 | Dihydro Myrcenol | 18479-58-8 | 2,6-Dimethyl-7-octen-2-ol | 2.16-20 | 3-9 | 5.2-7.8 |
| 30 | Tetra Hydro Linalool | 78-69-3 | 3,7-dimethyl-3-octanol | 3.5-30 | 5-16 | 8-12 |
| 31 | Verdox | 88-41-5 | (2-tert-butylcyclohexyl) acetate | 3-25 | 4-14 | 7.5-11 |
| 32 | Flor Acetate | 5413-60-5 | 3a,4,5,6,7,7a-hexahydro-4,7-methano-1H-inden-6-yl acetate | 5-40 | 8-25 | 14-17 |
| 33 | Laevo trisandol | 28219-61-6 | Ethyl trimethyl cyclopentene butenol | 0.1-7 | 0.25-5 | 0.5-3 |

Combinations

A. A perfume selected from the group consisting of:
   a) a first perfume comprising Table 1 perfume ingredients 1-46 in Range 1 of Table 1, preferably Range 2 of Table 1, more preferably Range 3 of Table 1;
   b) a second perfume comprising Table 2 perfume ingredients 1-34 in Range 1 of Table 2 preferably Range 2 of Table 2, more preferably Range 3 of Table 2;
   c) a third perfume comprising Table 3 perfume ingredients 1-46 in Range 1 of Table 3 preferably Range 2 of Table 3, more preferably Range 3 of Table 3;
   d) a fourth perfume comprising Table 4 perfume ingredients 1-33 in Range 1 of Table 4 preferably Range 2 of Table 4, more preferably Range 3 of Table 4; or
   e) a fifth perfume comprising Table 5 perfume ingredients 1-46 in Range 1 of Table 5 preferably Range 2 of Table 5, more preferably Range 3 of Table 5;
   with the proviso that the sum of said ingredients in each of said perfumes equals 100%.

B. A perfume according to Paragraph A selected from the group consisting of:
   a) a first perfume comprising Table 1 perfume ingredients 1-46 in Range 1 of Table 1, preferably Range 2 of Table 1, more preferably Range 3 of Table 1; or
   b) a second perfume comprising Table 2 perfume ingredients 1-34 in Range 1 of Table 2 preferably Range 2 of Table 2, more preferably Range 3 of Table 2.

C. A perfume according to Paragraph A selected from the group consisting of:
   a) a third perfume comprising Table 3 perfume ingredients 1-46 in Range 1 of Table 3 preferably Range 2 of Table 3, more preferably Range 3 of Table 3;
   b) a fourth perfume comprising Table 4 perfume ingredients 1-33 in Range 1 of Table 4 preferably Range 2 of Table 4, more preferably Range 3 of Table 4; or
   c) a fifth perfume comprising Table 5 perfume ingredients 1-46 in Range 1 of Table 5 preferably Range 2 of Table 5, more preferably Range 3 of Table 5.

D. A perfume delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, said perfume delivery system comprising a perfume selected from the perfumes described in Paragraphs A through C of the present specification.

E. A perfume delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, said perfume delivery system comprising a perfume selected from said first perfume described in Paragraphs A through C of the present specification.

F. A perfume delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, said perfume delivery system comprising a perfume selected from said second perfume described in Paragraphs A through C of the present specification.

G. A perfume delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, said perfume delivery system comprising a perfume selected from said third perfume described in Paragraphs A through C of the present specification.

H. A perfume delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, said perfume delivery system comprising a perfume selected from said fourth perfume described in Paragraphs A through C of the present specification.

I. A perfume delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, said perfume delivery system comprising a perfume selected from said fifth perfume described in Paragraphs A through C of the present specification.

J. A Polymer Assisted Delivery (PAD) system according to Paragraphs D through I, wherein said Polymer Assisted Delivery (PAD) system comprises a Polymer Assisted Delivery (PAD) Reservoir system.

K. The Polymer Assisted Delivery (PAD) Reservoir system of Paragraph J said Polymer Assisted Delivery (PAD) Reservoir system comprising a perfume delivery particle that comprises a shell material and a core material, said shell material encapsulating said core material, said core material comprising a perfume according to Paragraphs A through C and said shell comprising a material selected from the group consisting of polyethylenes; polyamides; polystyrenes; polyisoprenes; polycarbonates; polyesters; polyacrylates; aminoplasts, in one aspect said aminoplast comprises a polyureas, polyurethane, and/or polyureaurethane, in one aspect said polyurea comprises polyoxymethyleneurea and/or melamine formaldehyde; polyolefins; polysaccharides, in one aspect alginate and/or chitosan; gelatin; shellac; epoxy resins; vinyl polymers; water insoluble inorganics; silicone; and mixtures thereof.

L. The Polymer Assisted Delivery (PAD) Reservoir system of Paragraph K wherein said shell comprises melamine formaldehyde and/or cross linked melamine formaldehyde.

M. The Polymer Assisted Delivery (PAD) Reservoir system of Paragraph K wherein said shell is coated by a water-soluble cationic polymer selected from the group that consists of polysaccharides, cationically modified starch and cationically modified guar, polysiloxanes, dimethyldiallylammonium polyhalogenides, copolymers of dimethyldiallylammonium polychloride and vinyl pyrrolidone, acrylamides, imidazoles, imidazolinium halogenides and imidazolium halogenides and polyvinyl amine and its copolymers with N-vinyl formamide.

N. The Polymer Assisted Delivery (PAD) Reservoir system of Paragraph M wherein: said coating that coats said shell, comprises a cationic polymer and an anionic polymer.

O. The Polymer Assisted Delivery (PAD) Reservoir system of Paragraph N wherein said cationic polymer comprises hydroxyl ethyl cellulose; and said anionic polymer comprises carboxyl methyl cellulose.

P. The Polymer Assisted Delivery (PAD) Reservoir system of Paragraph K, wherein said perfume delivery particle is a perfume microcapsule.

Q. A consumer product comprising a perfume according to any of Paragraphs A through C and or a perfume delivery system according to any of Paragraphs D through P and a cleaning and/or treatment ingredient.

As disclosed, the benefits of the perfumes disclosed herein may be further enhanced by employing a perfume delivery system to apply such perfumes. Non-limiting examples of suitable perfume delivery systems, methods of making perfume delivery systems and the uses of such perfume delivery systems are disclosed in USPA 2007/0275866 A1. Such perfume delivery systems include:

Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

Matrix Systems: The fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are known that may control perfume release. Absorption and/or adsorption into or onto polymeric particles, films, solutions, and the like are aspects of this technology. Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, polyethylene, polyethylene terephthalate, polycyclohexylene dimethylene terephthalate, polycarbonate, polychloroprene, polyhydroxyalkanoate, polyketone, polyester, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded perfume associated with the polymer until the moment or moments of perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and releases it typically via perfume diffusion. The use of such equilibrium system polymers has the potential to decrease the odor intensity of the neat product (usually more so in the case of pre-loaded standard systems). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that perfume release occurs within the time frame of the application to impact the desired consumer touch point or touch points. Matrix systems also include hot melt adhesives and perfume plastics. In addition, hydrophobically modified polysaccharides may be formulated into the perfumed product to increase perfume deposition and/or modify perfume release. All such matrix systems, including for example polysaccarides and nanolatexes may be combined with other PDTs, including other PAD systems such as PAD reservoir systems in the form of a perfume microcapsule (PMC).

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP).

Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged. Scratch and sniff technologies are yet another example of PAD.

Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a CLogP greater than about 2.

Cyclodextrin (CD): This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit.

Starch Encapsulated Accord (SEA): The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid.

Zeolite & Inorganic Carrier (ZIC): This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Silica is another form of ZIC. Another example of a suitable inorganic carrier includes inorganic tubules, where the perfume or other active material is contained within the lumen of the nano- or micro-tubules. Preferably, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded perfume. Monomeric and/or polymeric materials, including starch encapsulation, may be used to coat, plug, cap, or otherwise encapsulate the PLT.

In one aspect, a perfume delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, wherein said perfume delivery system may comprise a perfume disclosed in this specification, for example a perfume selected from the perfumes disclosed in the perfume section of this specification, is disclosed.

In one aspect, a Polymer Assisted Delivery (PAD) system wherein said Polymer Assisted Delivery (PAD) system may comprise a Polymer Assisted Delivery (PAD) Reservoir system that may comprise a perfume disclosed in this specification, for example a perfume selected from the perfumes disclosed in the perfume section of this specification, is disclosed.

In one aspect of, said Polymer Assisted Delivery (PAD) Reservoir system said Polymer Assisted Delivery (PAD) Reservoir system may comprise a perfume delivery particle that may comprise a shell material and a core material, said shell material encapsulating said core material, said core material may comprise a perfume disclosed in this specification, for example a perfume selected from the perfumes disclosed in the perfume section of this specification, and said shell comprising a material selected from the group consisting of polyethylenes; polyamides; polystyrenes; polyisoprenes; polycarbonates; polyesters; polyacrylates; aminoplasts, in one aspect said aminoplast comprises a polyurea, polyurethane, and/or polyureaurethane, in one aspect said polyurea comprises polyoxymethyleneurea and/or melamine formaldehyde; polyolefins; polysaccharides, in one aspect alginate and/or chitosan; gelatin; shellac; epoxy resins; vinyl polymers; water insoluble inorganics; silicone; and mixtures thereof.

In one aspect, of said Polymer Assisted Delivery (PAD) Reservoir system said shell may comprise melamine formaldehyde and/or cross linked melamine formaldehyde.

In one aspect of said Polymer Assisted Delivery (PAD) Reservoir system said shell may be coated by a water-soluble cationic polymer selected from the group that consists of polysaccharides, cationically modified starch and cationically modified guar, polysiloxanes, dimethyldiallylammonium polyhalogenides, copolymers of dimethyldiallylammonium polychloride and vinyl pyrrolidone, acrylamides, imidazoles, imidazolinium halogenides and imidazolium halogenides and polyvinyl amine and its copolymers with N-vinyl formamide.

In one aspect of said Polymer Assisted Delivery (PAD) Reservoir system said coating that coats said shell, may comprise a cationic polymer and an anionic polymer.

In one aspect of said Polymer Assisted Delivery (PAD) Reservoir system wherein said cationic polymer may comprise hydroxyl ethyl cellulose; and said anionic polymer may comprise carboxyl methyl cellulose.

In one aspect, said Polymer Assisted Delivery (PAD) Reservoir system is a perfume microcapsule.

Process of Making Encapsulates

In one aspect, a process that may comprise:
- a.) preparing a first solution that may comprise, based on total solution weight from about 20% to about 90%, from about 40% to about 80%, or even from about 60% to about 80% water, of a first emulsifier and a first resin, the ratio of said first emulsifier and said first resin being from about 0.1:0 to about 10:0, from about 0.1:1 to about 10:1, from about 0.5:1 to about 3:1, or even from about 0.8:1 to about 1.1:1;
- b.) preparing a second solution that may comprise based on total solution weight from about 20% to about 95% water, of a second emulsifier and a second resin, the ratio of said second emulsifier and said second resin being from about 0:1 to about 3:1, from about 0.04:1 to about 0.2:1, or even from about 0.05:1 to about 0.15:1;
- c.) combining a core material that may comprise a perfume selected from the perfumes described in Paragraphs A through C of the present specification and said first solution to form a first composition;
- d.) emulsifying said first composition;
- e.) combining said first composition and said second solution to form a second composition and optionally combining any processing aids and said second composition—said first composition and said second solution may be combined in any order but in one aspect said second solution is added to said first composition or said second solution and said first composition are combined simultaneously;
- f.) mixing said second composition for at least 15 minutes, at least 1 hour or even from about 4 hours to about 100 hours at a temperature of from about 25° C. to about 100° C., from about 45° C. to about 90° C., or even from about 50° C. to about 80° C. heat and optionally combining any processing aids to said second composition;
- g.) optionally combining any scavenger material, structurant, and/or anti-agglomeration agent with said second composition during step f.) or thereafter—such materials may be combined in any order but in one aspect the scavenger material is combined first, any structurant second, and then anti-agglomeration agent is combined; and
- h.) optionally spray drying said second composition is disclosed.

In one or more aspects of the process, said first and second resins may comprise the reaction product of an aldehyde and an amine, suitable aldehydes include, formaldehyde. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof.

In one or more aspects of the process, said first and second emulsifiers may comprise a moiety selected from the group consisting of carboxy, hydroxyl, thiol, amine, amide and combinations thereof. In one aspect, said emulsifier may have a pKa of less than 5, preferably greater than 0 but less than 5. Emulsifiers include acrylic acid-alkyl acrylate copolymer, poly(acrylic acid), polyoxyalkylene sorbitan fatty esters, polyalkylene co-carboxy anhydrides, polyalkylene co-maleic anhydrides, poly(methyl vinyl ether-co-maleic anhydride), poly(propylene-co-maleic anhydride), poly(butadiene co-maleic anhydride), and poly(vinyl acetate-co-maleic anhydride), polyvinyl alcohols, polyalkylene glycols, polyoxyalkylene glycols, and mixtures thereof.

In one or more aspects of the process, the pH of the first and second solutions may be controlled such that the pH of said first and second solution is from about 3.0 to 7.0.

In one or more aspects of the process, during step f.), from about 0% to about 10%, from about 1% to about 5% or even from about 2% to about 4%, based on total second composition weight, of a salt comprising an anion and cation, said anion being selected from the group consisting of chloride, sulfate, phosphate, nitrate, polyphosphate, citrate, maleate, fumarate and mixtures thereof; and said cation being selected from the group consisting of a Periodic Group IA element, Periodic Group IIA element, ammonium cation and mixtures thereof, preferably sodium sulfate, may be combined with said second composition.

In one or more aspects of the process, any of the aforementioned processing parameters may be combined.

Supplemental teachings of making suitable encapsulates as well as suitable shell materials are described in U.S. Pat. No. 6,869,923 B1 and US Published Patent Applications Nos. 2005/0276831 A1 and 2007/020263 A1. Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Compositions

In one aspect, a composition that may comprise any aspect of the perfume delivery systems and/or perfumes disclosed in the present specification is disclosed.

In one aspect, said composition may be a consumer product.

In one aspect, such composition may be a consumer product that may comprise, based on total composition weight, from about 0.001% to about 50%, from about 0.01% to about 10%, or even from about 0.1% to about 5%, of a perfume disclosed in the present specification—from about 0.001% to about 90%, from about 0.01% to about 50%, or even from about 0.1% to about 10%, of said perfume, based on said perfume's weight, may be provided by a perfume delivery system according to the present specification.

In one aspect, said composition may comprise an encapsulate wherein said encapsulate's density may be such that the density ratio of said encapsulate to one or more fluids of the composition's fluids may be from about 0.9:1 to about 1.1:1; from about 0.98:1 to about 1.02:1; from about 0.99:1 to about 1.01:1 or even 1:1.

In one aspect, any of the aforementioned compositions may comprise a cleaning and/or treatment ingredient.

In one aspect, any of the aforementioned compositions' encapsulates may be a perfume microcapsule.

In one aspect, any of the aforementioned compositions may comprise one or more cleaning and/or treatment agents selected from the adjunct ingredients listed in the present specification.

While the precise level of encapsulate that is employed depends on the type and end use of the consumer product, in one aspect a consumer product may comprise, based on total composition weight, at least about 0.01%, from about 0.01% to about 80%, or even from about 0.02% to about 10% wt % of a encapsulate disclosed herein.

In one aspect, a consumer product that is compact is disclosed.

In one aspect, a consumer products including liquid detergents having a water content, based on total consumer product formulation weight, of from about 0% to about 15%, from about 0.01% to about 15%, from about 0.5% to about 10% or even from about 1% to about 8% water are disclosed.

In one aspect, the consumer product is a cleaning and/or treatment composition or fabric care composition that may comprise an encapsulate disclosed in the present specification and at least one cleaning and/or treatment composition or fabric care adjunct ingredient.

In one aspect, a cleaning composition may comprise, from about 0.005% to about 5% weight % of such encapsulate based on total cleaning composition weight of such encapsulate. In one aspect, a fabric treatment composition may comprise, based on total fabric treatment composition weight from about 0.005% to about 20% of such encapsulate.

Aspects of the invention include the use of the encapsulates of the present invention in detergent compositions (e.g., TIDE™), hard surface cleaners (e.g., MR CLEAN™), automatic dishwashing liquids (e.g., CASCADE™), dishwashing liquids (e.g., DAWN™), and floor cleaners (e.g., SWIFFER™). The cleaning compositions disclosed herein may be formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 2 to about 11. Techniques for controlling pH at recommended usage levels include the use of buffers, alkalis, acids, etc., and are well known to those skilled in the art.

Fabric treatment compositions disclosed herein typically comprise a fabric softening active ("FSA"). Suitable fabric softening actives, include, but are not limited to, materials selected from the group consisting of quats, amines, fatty esters, sucrose esters, silicones, dispersible polyolefins, clays, polysaccharides, fatty oils, polymer latexes and mixtures thereof.

Formaldehyde Scavenger

In one aspect, the perfume delivery system disclosed herein may be combined with a formaldehyde scavenger. In one aspect, such perfume delivery system may comprise the encapsulates of the present invention. Suitable formaldehyde scavengers include materials selected from the group consisting of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(l-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or a mixture thereof. These formaldehyde scavengers may be obtained from Sigma/Aldrich/Fluka of St. Louis, Mo. U.S.A. or PolySciences, Inc. of Warrington, Pa., U.S.A.

Such formaldehyde scavengers are typically combined with a slurry containing said benefit agent containing delivery particle, at a level, based on total slurry weight, of from about 2 wt. % to about 18 wt. %, from about 3.5 wt. % to about 14 wt. % or even from about 5 wt. % to about 13 wt. %.

In one aspect, such formaldehyde scavengers may be combined with a product containing a benefit agent containing delivery particle, said scavengers being combined with said product at a level, based on total product weight, of from about 0.005% to about 0.8%, alternatively from about 0.03% to about 0.5%, alternatively from about 0.065% to about 0.25% of the product formulation.

Adjunct Materials

While not essential for each consumer product embodiment of the present invention, the non-limiting list of adjuncts illustrated hereinafter are suitable for use in the instant consumer products and may be desirably incorporated in certain embodiments of the invention, for example to assist or enhance performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the operation for which it is to be used. Such adjunct are in addition to the perfumes and/or perfume delivery systems previously disclosed herein. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, thickeners/structurants, fabric softeners, carriers, hydrotropes, processing aids and/or pigments.

As stated, the adjunct ingredients are not essential for each consumer product embodiment of the present invention. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, thickeners/structurants, fabric softeners, carriers, hydrotropes, processing aids and/or pigments. However, when one or more adjuncts is present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders, polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof.

If desired, the compositions herein can be catalyzed by means of a manganese compound. Such compounds and levels of use are well known in the art.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Rheology Modifier

The liquid compositions of the present invention may comprise a rheology modifier. The rheology modifier may be selected from the group consisting of non-polymeric crystalline, hydroxy-functional materials, polymeric rheology modifiers which impart shear thinning characteristics to the aqueous liquid matrix of the composition. In one aspect, such rheology modifiers impart to the aqueous liquid composition a high shear viscosity, at 20 sec$^{-1}$ shear rate and at 21° C., of from 1 to 7000 cps and a viscosity at low shear (0.5 sec$^{-1}$ shear rate at 21° C.) of greater than 1000 cps, or even 1000 cps to 200,000 cps. In one aspect, for cleaning and treatment compositions, such rheology modifiers impart to the aqueous liquid composition a high shear viscosity, at 20 sec$^{-1}$ and at 21° C., of from 50 to 3000 cps and a viscosity at low shear (0.5 sec$^{-1}$ shear rate at 21° C.) of greater than 1000 cps, or even 1000 cps to 200,000 cps. Viscosity according to the present invention is measured using an AR 2000 rheometer from TA instruments using a plate steel spindle having a plate diameter of 40 mm and a gap size of 500 μm. The high shear viscosity at 20 sec$^{-1}$ and low shear viscosity at 0.5 sec$^{-1}$ can be obtained from a logarithmic shear rate sweep from 0.1 sec$^{-1}$ to 25 sec$^{-1}$ in 3 minutes time at 21° C. Crystalline hydroxyl functional materials are rheology modifiers which form thread-like structuring systems throughout the matrix of the composition upon in situ crystallization in the matrix. Polymeric rheology modifiers are preferably selected from polyacrylates, polymeric gums, other non-gum polysaccharides, and combinations of these polymeric materials.

Generally the rheology modifier will comprise from 0.01% to 1% by weight, preferably from 0.05% to 0.75% by weight, more preferably from 0.1% to 0.5% by weight, of the compositions herein.

Structuring agents which are especially useful in the compositions of the present invention may comprise non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. In one aspect, rheology modifiers include crystalline, hydroxyl-containing rheology modifiers include castor oil and its derivatives. In one aspect, rheology modifiers include hydrogenated castor oil derivatives such as hydrogenated castor oil and hydrogenated castor wax. Commercially available, castor oil-based, crystalline, hydroxyl-containing rheology modifiers include THIXCIN™ from Rheox, Inc. (now Elementis).

Other types of rheology modifiers, besides the non-polymeric, crystalline, hydroxyl-containing rheology modifiers described heretofore, may be utilized in the liquid detergent compositions herein. Polymeric materials which provide shear-thinning characteristics to the aqueous liquid matrix may also be employed.

Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum.

If polymeric rheology modifiers are employed herein, a preferred material of this type is gellan gum. Gellan gum is a heteropolysaccharide prepared by fermentation of Pseudomonaselodea ATCC 31461. Gellan gum is commercially marketed by CP Kelco U.S., Inc. under the KELCO-GEL tradename.

A further alternative and suitable rheology modifier include a combination of a solvent and a polycarboxylate polymer. More specifically the solvent may be an alkylene glycol. In one aspect, the solvent may comprise dipropylene glycol. In one aspect, the polycarboxylate polymer may comprise a polyacrylate, polymethacrylate or mixtures thereof. In one aspect, solvent may be present, based on total composition weight, at a level of from 0.5% to 15%, or from 2% to 9% of the composition. In one aspect, polycarboxylate polymer may be present, based on total composition weight, at a level of from 0.1% to 10%, or from 2% to 5%. In one aspect, the solvent component may comprise mixture of dipropylene glycol and 1,2-propanediol. In one aspect, the ratio of dipropylene glycol to 1,2-propanediol may be 3:1 to 1:3, or even 1:1. In one aspect, the polyacrylate may comprise a copolymer of unsaturated mono- or di-carbonic acid and $C_1$-$C_{30}$ alkyl ester of the (meth) acrylic acid. In another aspect, the rheology modifier may comprise a polyacrylate of unsaturated mono- or di-carbonic acid and $C_1$-$C_{30}$ alkyl ester of the (meth) acrylic acid. Such copolymers are available from Noveon Inc under the tradename Carbopol Aqua 30®.

In the absence of rheology modifier and in order to impart the desired shear thinning characteristics to the liquid composition, the liquid composition can be internally structured through surfactant phase chemistry or gel phases.

Processes of Making and Using Consumer Products

The embodiments of consumer products of the present invention can be formulated into any suitable form and prepared by any process chosen by the formulator, non-limiting examples of which are described in U.S. Pat. No. 5,879,584; which is incorporated herein by reference.

In one aspect, the perfumes and/or delivery systems comprising same that are disclosed herein may be incorporated into solid particles, particularly polymeric based particles. Preferably said perfume delivery system is a microcapsule that comprises said perfume one or more of said perfumes. Examples of such polymeric particles may include particles comprising polyethylene glycol, starches and polysaccharides, polyvinyl alcohol, celluloses. Such particles may additionally comprise additional components such as other benefit agents, inorganic fillers such as carbonate, silicate, clay, metal oxides. Particularly useful particles include particles based on polyethylene glycol.

Method of Use

Compositions, such as consumer products, containing the encapsulate disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with an encapsulate according to the present invention or composition comprising said encapsulate and then optionally washed and/or rinsed. For purposes of the present invention, washing includes but is not limited to, scrubbing, and mechanical agitation. The situs may comprise most any material, for example a fabric, fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

A method of treating and/or cleaning a situs, said method comprising
 a) optionally washing and/or rinsing said situs;
 b) contacting said situs with a perfume according to any of Paragraphs A through C, perfume delivery system according to any of Paragraphs D through P, and/or a consumer product according to Paragraph Q; and
 c) optionally washing and/or rinsing said situs.

The drying may be passive like line drying and/or active such as in a dryer.

A situs treated with a composition selected from the compositions of a perfume according to any of Paragraphs A through C, perfume delivery system according to any of Paragraphs D through P, and/or a consumer product according to Paragraph Q.

Method for Determining Performance

Product Preparation and Washtest

Prepare liquid detergent products and fabric enhancer products containing 0.8% (as 100% active) perfume oil (either free or encapsulated)

Products are used to run a full scale wash in Miele Softronic W1714 washing machine.

For the test 3 kg ballast load is used. The load consists of 600 g polyester, 600 g polycotton, 600 g muslin (flat) cotton, 600 g knitted cotton and 600 g terry towels.

Ballast loads are preconditioned in Miele Softronic W1714 washing machine by running a short cotton cycle wash at 95° C. In total 4 runs are done: 2 runs where 70 g unperfumed powder is added in dispenser followed by 2 runs without detergent.

After preconditioning the ballast loads are tumble dried.

For each washtest 12 small terry tracers (100% cotton, 30×30 cm) are added into the washing machine. These tracers are preconditioned in same way as ballast load (50 terry tracers per washing machine).

Before running the test washing machines are boiled out using a cotton cycle run at 95° C.

Liquid Detergent Washtest

Two legs are run:

A=Liquid detergent+0.8% perfume oil

B=Liquid detergent+0.8% encapsulated perfume oil

Washtest is run in WE Miele Softronic W1714 washing machine, wash cycle is short crease recovery cycle at 30° C. and a spin speed of 1000 rpm.

Put ballast load and terry tracers in washing machine, on top place dosing ball with liquid detergent (products dosage=67.7 g)

Run wash cycle. After wash remove terry tracers from washing machine.

Liquid Fabric Enhancer Washtest

Two legs are run:

C=Liquid fabric enhancer+0.8% perfume oil

D=Liquid fabric enhancer+0.8% encapsulated perfume oil

Washtest is run in WE Miele Softronic W1714 washing machine, wash cycle is short cotton cycle wash at 60° C. and a spin speed of 1000 rpm.

Put ballast load and terry tracers in washing machine. In dispenser add 40 g unperfumed powder. Run wash cycle. When last rinse starts add in dispenser liquid fabric enhancer product (25 ml liquid fabric enhancer product prediluted in 2 liter city water)

After wash remove terry tracers from washing machine.

Terry tracers are submitted for olfactive evaluation to perfumers. Tracers are evaluated on wet fabric odor, after 1 day line drying and after rubbing the fabric by using Primavera scale (intensity scale from 0-100)

Wet and 1 day line dried terry tracers are submitted for headspace analysis.

1 day line dried tracers are submitted for deposition analysis.

Headspace Analysis

Wet and dry fabric samples, originating from rinse/wash cycles, were analyzed by fast headspace GC/MS approach. 4×4 cm part of the terry cotton tracers were transferred to 25 ml headspace vials. The fabric samples were equilibrated for 10 minutes@ 75° C. The headspace above the fabrics was sampled via SPME (50/30 μm DVB/Carboxen/PDMS) approach for 5 minutes. The SPME fibre was subsequently on-line thermally desorbed into the GC. The analytes were analyzed by fast GC/MS in full scan mode. Ion extraction of the specific masses of the PRM's was used to calculate the total headspace response (expressed in area counts) and perfume headspace composition above the tested legs.

Instrumental Conditions I 0150

Combipal configured for automated SPME 10 minutes incubation time @ 75° C.

5 minutes SPME extraction time

SPME fibre: 50/30 micron DVB/Carboxen/PDMS (Supelco 57328-U)

GC/MS Analysis

Fast GC/MS:

Column: $CPSIL_5$ $CB_{15}$ m×0.15 mm×0.15 micrometer (Varian)

Oven program: 40 C (0.5 min)–40 C/min–280 C (0 min)

MSD: Full scan mode (extraction of specific ions for quantification)

Deposition Analysis

Per leg 4 replicates are run.

Cut small pieces of terry tracers and add into glass jars (210 ml). Per leg 4 terry tracers are available. Per tracer 3 pieces of fabric are cut and added into the glass jar. Fabric weight per jar is between 3.00 g and 4.00 g and is recorded per replicate.

Benzophenone=weigh+/−50 mg in 10 mL MeOH (record the exact weight)

500×dil Benz 1

100×dil Benz 2

Fabric samples in jar+2.5 uL 500×dil Benz 1+50 mL MeOH+50 uL HCOOH

Shake for 2 hours @ 60° C. @ 150 rpm

Calibration Curve:

Oil std=25 uL=(record the weight) . . . mg in 10 mL MeOH

100×dil oil 1 uL–5 uL–10 uL–25 uL–50 uL–1 ul std–3 uL std+5 uL 100×dil Benz 2

Take an aliquot of the jar solution and put them in an MS vial. This is measured with the method developed for this specific perfume accord on the API 3000 in APCI mode (positive MRM scan) with methanol as eluent

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1: 84 wt % Core/16 wt % Wall Melamine Formaldehyde (MF) Capsule 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil according to Table 1 or Table 2 is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Mo., U.S.A.) is added to the suspension. An average capsule size of 30 um is obtained as analyzed by a Model 780 Accusizer.

Example 2

To demonstrate the benefit of the present invention, Applicants prepared liquid detergent matrix A, below.

| Active Material in weight % | A |
|---|---|
| $C_{14}$-$C_{15}$ alkyl poly ethoxylate 7 | 3.39 |
| $C_{12}$-$C_{14}$ alkyl poly ethoxylate 7 | 1.13 |
| $C_{12}$-$C_{14}$ alkyl poly ethoxylate 3 sulfate Na salt | 7.66 |
| Alkylbenzene sulfonic acid | 1.17 |
| Citric Acid | 2.73 |
| $C_{12-18}$ fatty acid | 5.06 |
| Enzymes | 0.2 |
| Boric Acid | 1.40 |
| Trans-sulphated ethoxylated hexamethylene diamine quat | 0.81 |
| Diethylene triamine penta methylene phosphonic acid | 0.12 |
| Hydrogenated Castor Oil structurant | 0.300 |
| Ethanol | 1.59 |
| 1,2 propanediol | 0.07 |
| Sodium hydroxide | 3.48 |
| Silicone PDMS emulsion | 0.0025 |
| Blue Dye | 0.0006 |
| Preservative Acticide MBS 2550 (ex Thor) | 0.0135 |
| Perfume according to Table 1 or Table 2 | 0.34 |
| Merquat 5300 polymer (1) | 0.19 |
| Water | Balance to 100% |

(1) Merquat 5300: terpolymer with mole ratio: 90% PAM/5% AA/5% MAPTAC produced by Nalco.

Examples 3-10

Examples of laundry detergent compositions comprising the perfume composition are included below.

| Raw material | % w/w of laundry detergent compositions | | | | | | | |
|---|---|---|---|---|---|---|---|---|
| | 3 | 4 | 5 | 6 | 7 | 8 | 9 | 10 |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Microcapsules of Example 1 | 1.4 | 0.6 | 0.8 | 1.0 | 0.7 | 0.3 | 0.7 | 1.2 |
| Water & Miscellaneous | Balance to 100% | | | | | | | |

Examples 11

Examples of granular laundry detergent compositions comprising the perfume composition are included below.

| Raw material | % w/w of laundry detergent compositions | | | | | | | |
|---|---|---|---|---|---|---|---|---|
| | 11 | 12 | 13 | 14 | 15 | 16 | 17 | 18 |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |

-continued

| Raw material | % w/w of laundry detergent compositions | | | | | | | |
|---|---|---|---|---|---|---|---|---|
| | 11 | 12 | 13 | 14 | 15 | 16 | 17 | 18 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Microcapsules of Example 1 | 1.4 | 0.6 | 0.8 | 1.0 | 0.7 | 0.3 | 0.7 | 1.2 |
| Water & Miscellaneous | Balance to 100% | | | | | | | |

The equipment and materials described in Examples 1 through to 18 can be obtained from the following: IKA Werke GmbH & Co. KG, Staufen, Germany; CP Kelco, Atlanta, United States; Forberg International AS, Larvik, Norway; Degussa GmbH, Dusseldorf, Germany; Niro A/S, Soeberg, Denmark; Baker Perkins Ltd, Peterborough, United Kingdom; Nippon Shokubai, Tokyo, Japan; BASF, Ludwigshafen, Germany; Braun, Kronberg, Germany; Industrial Chemicals Limited, Thurrock, United Kingdom; Primex ehf, Siglufjordur, Iceland; ISP World Headquarters; Polysciences, Inc. of Warrington, Pa., United States; Cytec Industries Inc., New Jersey, United States; International Specialty Products, Wayne, N.J., United States; P&G Chemicals Americas, Cincinnati, Ohio, United States; Sigma-Aldrich Corp., St. Louis, Mo., United States, Dow Chemical Company of Midland, Mich., USA Examples 18-27: Fabric Conditioner Non-limiting examples of fabric conditioners containing the polymer coated perfume microcapsules disclosed in the present specification are summarized in the following table.

| (% wt) | EXAMPLES | | | | | | | | | |
|---|---|---|---|---|---|---|---|---|---|---|
| | 18 | 19 | 20 | 21 | 22 | 23 | 24 | 25 | 26 | 27 |
| FSA [a] | 14 | 16.47 | 14 | 12 | 12 | 16.47 | — | — | 5 | 10 |
| FSA [b] | | | | | | | 3.00 | — | — | — |
| FSA [c] | | | | | | | — | 6.5 | — | — |
| Ethanol | 2.18 | 2.57 | 2.18 | 1.95 | 1.95 | 2.57 | — | — | 0.81 | — |
| Isopropyl Alcohol | — | — | — | — | — | — | 0.33 | 1.22 | — | 1.0— |
| Starch [d] | 1.25 | 1.47 | 2.00 | 1.25 | — | 2.30 | 0.5 | 0.70 | 0.71 | 0.42 |
| Phase Stabilizing Polymer [f] | 0.21 | 0.25 | 0.21 | 0.21 | 0.14 | 0.18 | 0.15 | 0.14 | 0.2 | 0.1 |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | 0025. |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Perfume microcapsules as disclosed in Example 1 | 0.2 | 0.02 | 0.1 | 0.15 | 0.12 | 0.13 | 0.3 | 0.4 | 0.24 | 0.1 |
| Additional Neat Perfume according to Table 1 or Table 2 | 0.8 | 0.7 | 0.9 | 0.5 | 1.2 | 0.5 | 1.1 | 0.6 | 1.0 | 0.9 |

|  | EXAMPLES | | | | | | | | | |
| --- | --- | --- | --- | --- | --- | --- | --- | --- | --- | --- |
| (% wt) | 18 | 19 | 20 | 21 | 22 | 23 | 24 | 25 | 26 | 27 |
| Deionized Water | † | † | † | † | † | † | † | † | † | † |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Rheovis DCE ex BASF.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
† balance Examples 28-33 Liquid Laundry Formulations (HDLs)

| Ingredient | 28 | 29 | 30 | 31 | 32 | 33 |
| --- | --- | --- | --- | --- | --- | --- |
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1, 2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Neat Perfume according to Table 1 or 2 | 0.02 | 0.15 | 0.0 | 0.2 | 0.3 | 0.1 |
| Perfume microcapsules as disclosed in Example 1 | 0.2 | 0.02 | 0.1 | 0.15 | 0.12 | 0.13 |
| Water | Balance | Balance | Balance | Balance | Balance | Balance |

Examples 34-41: Liquid Unit Dose

The following are examples of unit dose executions wherein the liquid composition is enclosed within a PVA film. The preferred film used in the present examples is Monosol M8630 76 μm thickness.

| | D 3 compartments | | | E 2 compartments | | F 3 compartments | | |
|---|---|---|---|---|---|---|---|---|
| | \multicolumn{8}{c}{Compartment #} | | | | | | | |
| | 34 | 35 | 36 | 37 | 38 | 39 | 40 | 41 |
| | \multicolumn{8}{c}{Dosage (g)} | | | | | | | |
| | 34.0 | 3.5 | 3.5 | 30.0 | 5.0 | 25.0 | 1.5 | 4.0 |
| Ingredients | \multicolumn{8}{c}{Weight %} | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | | 0.4 | | |
| Brightener | 0.2 | 0.2 | 0.2 | 0.3 | | 0.3 | | |
| Perfume Microcapsules as Example 1 | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume according to Table 1 or 2 | 1.7 | 1.7 | | 0.6 | | 1.5 | 0.5 | |
| Minors (antioxidant, sulfite, aesthetics, . . .) | 2.0 | 2.0 | 2.0 | 4.0 | 1.5 | 2.2 | 2.2 | 2.0 |
| Buffers (sodium carbonate, monoethanolamine) [3] | \multicolumn{8}{c}{To pH 8.0 for liquids} | | | | | | | |
| | \multicolumn{8}{c}{To RA > 5.0 for powders} | | | | | | | |
| Solvents (1,2 propanediol, ethanol), Sulfate | \multicolumn{8}{c}{To 100 p} | | | | | | | |

Polyethylenimine (MW = 600) with 20 ethoxylate groups per —NH.

[3] RA = Reserve Alkalinity (g NaOH/dose)

Example 42 Shampoo Formulation

| Ingredient | |
|---|---|
| Ammonium Laureth Sulfate (AE3S) | 6.00 |
| Ammonium Lauryl Sulfate (ALS) | 10.00 |
| Laureth-4 Alcohol | 0.90 |
| Trihydroxystearin | 0.10 |
| Perfume microcapsules as disclosed in Example 1 | 0.60 |
| Sodium Chloride | 0.40 |
| Citric Acid | 0.04 |
| Sodium Citrate | 0.40 |
| Sodium Benzoate | 0.25 |
| Ethylene Diamine Tetra Acetic Acid | 0.10 |
| Dimethicone | 1.00 |
| Water and Minors (QS to 100%) | Balance |

Example 43

Examples of free flowing particles products that comprise perfume and/or microcapsules comprising such perfume are provided below. The table below also exemplifies combinations which comprise also perfume free and in microcapsules or combinations of these with aforementioned combinations with malodor reduction materials and/or compositions. The table also exemplifies compositions having only malodor reduction materials and/or compositions free, in microcapsules and combinations thereof that have little to no fragrance to provide a product that is essentially 'fragrance free'

| | COMPOSITION | | | |
|---|---|---|---|---|
| | 1 | 2 | 3 | 4 |
| Component | % Wt Active | % Wt Active | % Wt Active | % Wt Active |
| Polyethylene glycol | 70-99 | 0-20 | 0-29 | 0-40 |
| Clay | 0-29 | 0-20 | 0-20 | 0-10 |
| NaCl | 0-29 | 50-99 | 0-29 | 0-40 |
| Na2SO4 | 0-10 | 0-10 | 0-10 | 0-5 |
| Urea | 0-29 | 0-29 | 0-99 | 0-40 |
| Polysaccharide | 0-29 | 0-29 | 0-29 | 0-5 |
| Zeolite | 0-29 | 0-29 | 0-29 | 0-5 |
| Plasticizers/Solvents | | | | |
| Starch/Zeolite | 0-29 | 0-29 | 0-29 | 0-5 |
| Silica | 0-5 | 0-5 | 0-5 | 0-5 |
| Metal oxide | 0-29 | 0-29 | 0-29 | 0-29 |
| Metal catalyst | 0.001-0.5 | 0.001-0.5 | 0.001-0.5 | 0.001-0.5 |
| Opacifier | 0-5 | 0-5 | 0-1 | 0-1 |
| Water | 0-2 | 0-2 | 0-5 | 0-5 |
| Perfume as provided in Tables 1 & 2 | 0-5 | 0-5 | 0-5 | 0-5 |
| Microcapsules comprising perfume according to Tables 1 or 2 | 0.001-10 | 0.001-4.5 | 0.001-3 | 0.001-7.5 |

| | COMPOSITION | | | |
|---|---|---|---|---|
| | 5 | 6 | 7 | 8 |
| Component | % Wt Active | % Wt Active | % Wt Active | % Wt Active |
| Polyethylene glycol | 70-99 | 0-20 | 0-29 | 0-40 |
| Clay | 0-29 | 0-20 | 0-20 | 0-10 |
| NaCl | 0-29 | 50-99 | 0-29 | 0-40 |
| Na2SO4 | 0-10 | 0-10 | 0-10 | 0-5 |
| Urea | 0-29 | 0-29 | 0-99 | 0-40 |
| Polysaccharide | 0-29 | 0-29 | 0-29 | 0-5 |
| Zeolite | 0-29 | 0-29 | 0-29 | 0-5 |
| Plasticizers/Solvents | | | | |
| Starch/Zeolite | 0-29 | 0-29 | 0-29 | 0-5 |
| Silica | 0-5 | 0-5 | 0-5 | 0-5 |
| Metal oxide | 0-29 | 0-29 | 0-29 | 0-29 |
| Metal catalyst | 0.001-0.5 | 0.001-0.5 | 0.001-0.5 | 0.001-0.5 |
| Opacifier | 0-5 | 0-5 | 0-1 | 0-1 |
| Water | 0-2 | 0-2 | 0-5 | 0-5 |
| Microcapsules comprising perfume according to Tables 1 or 2 | 0.001-10 | 0.001-4.5 | 0.001-3 | 0.001-7.5 |

(1) PEG
(2) Clay
(3) Urea
(4) Polysaccharide, mostly starches, unmodified starches, starch derivatives, acid-modified starch and kappa carrageenan
(5) Zeolite
(6) Starch/Zeolite - SEA
(7) Metal oxides - non-limiting examples - TiO2, ZnO, MnO
(8) Metal catalysts
(9) Opacifier Example 44 Aqueous Composition/Fabric Refresher or Air Freshening Composition The aqueous composition of the present invention comprises a perfume mixture and an aqueous carrier. The final pH of the aqueous composition herein may be from about 1 to about 11, alternatively from about 3 to about 10, alternatively from about 4 to about 8.

Perfume

The perfume is the perfume as provided in Tables 1 & 2 of this specification.

Flavorants

In one embodiments, the aqueous composition is substantially free of or free of a flavorant. A flavorant is an edible chemical that is added to food and beverage products to alter the taste of the food or beverage product. Where a perfume mixture is free of a flavorant, the perfume mixture is free of flavorants including perfume materials that are known to be used as flavorants in the food and beverage industry. Having a perfume mixture that is free of flavorants can help provide improved hedonic benefits of the aqueous composition.

Aqueous Carrier

The aqueous composition of the present invention also comprises an aqueous carrier. The aqueous carrier which is used may be distilled, deionized, or tap water. Water may be present in any amount for the composition to be aqueous. In some embodiments, water may be present in an amount of about 70% to about 99.9%, or about 80% to about 99.9%, or about 85% to 99.9%, or about 90% to about 99.5%, or about 92% to about 99.5%, or about 95%, by weight of said aqueous composition.

Optional Ingredients

The aqueous composition may also have less than about 30%, or less than about 10%, or less than about 5%, by weight of the composition, of alcohol. However, the volatile low molecular weight monohydric alcohols such as ethanol and/or isopropanol should be limited since these volatile organic compounds may contribute both to flammability problems and environmental pollution problems. If small amounts of low molecular weight monohydric alcohols (e.g., ethanol, methanol, and isopropanol, or polyols, such as ethylene glycol and propylene glycol) are present in the composition of the present invention due to the addition of these alcohols to such things as perfumes and as stabilizers for some preservatives, the level of monohydric alcohol may be about 1% to about 5%, alternatively less than about 5%, by weight of the aqueous composition.

The aqueous perfume composition of the present invention may be formulated into a fabric refresher or air freshening composition comprising malodor counteractants, particulate controlling polymers, emulsifiers and solubilizing surfactants to solubilize any excess hydrophobic organic materials, particularly any perfume materials. Other emulsifiers, solvents, solubilizers and surfactants as described in U.S. Pat. No. 7,998,403 or in US 2012/0288448A1 can be used to enhance performance of the aqueous composition. A suitable solubilizing surfactant, is a no-foaming or low-foaming surfactant. In one embodiment, the aqueous composition contains ethoxylated hydrogenated castor oil. One suitable hydrogenated castor oil is Basophor™, available from BASF. The solubilizer to perfume ratio in aqueous perfume composition may be about 2:1 or greater than 2:1.

An exemplary aqueous composition is shown in the Table below

| | |
|---|---|
| Water | 93% |
| Alcohol | 5% |
| Surfactants & Emulsifiers | 1.9% |
| Buffers & Other Stabilizers | 0.1% |

Olfactive Data for Perfume Microcapsules Comprising Melamine Formaldehyde Based Shells

| Code | Product details | WFO | 1 day DFO | 1 day DFO rubbed |
|---|---|---|---|---|
| A | Liquid laundry detergent with 0.8% perfume according to table 1 | 42.5 | 25 | n/a |
| B | Liquid laundry detergent with 0.8% encapsulated perfume according to table 1 | 37.5 fruity green | 42.5 very strong | 52.5 (+10) fruity, green, citrus |
| C | Liquid fabric enhancer with 0.8% perfume according to table 1 | 50 overall character more complex versus A | 25 | n/a |
| D | Liquid fabric enhancer with 0.8% encapsulated perfume according to table 1 | 37.5 sweet fruity | 37.5 less strong versus B | 50 (+12.5) fruity, sweet, watery |

WFO = Wet Fabric Odor
DFO = Dry Fabric Odor

Conclusions:
The overall perfume of the microcapsules is sweeter in the liquid fabric enhancer than in the liquid laundry detergent.
The profile is noticeably more green/citrus in character in the liquid laundry detergent.

Olfactive Data for Perfume Microcapsules Comprising Polyacrylate Based Shells

| Code | Product details | WFO | 1 day DFO | 1 day DFO rubbed |
|---|---|---|---|---|
| A | Liquid laundry detergent with 0.8% perfume according to table 1 | 72.5 Very strong | 25 | n/a |
| B | Liquid laundry detergent with 0.8% encapsulated perfume according to table 1 | 72.5 green, vegetable | 35 fruity watery, less complex/D | 50 (+15) Fruity |
| C | Liquid fabric enhancer with 0.8% perfume according to table 1 | 70 less harsh/A&B | 25 | n/a |
| D | Liquid fabric enhancer with 0.8% encapsulated perfume according to table 1 | 72.5 vegetable, melon, softer in character | 50 fruity, water melon, floral violet | 65 (+15) fruity, floral violet |

Headspace Data Olfactive Data for Perfume Microcapsules Comprising Melamine Formaldehyde Based Shells
Headspace Data—Perfume Raw Materials Release in Headspace from Damp Fabrics

| Component name | Liquid laundry detergent + 0.8% perfume according to the invention Area | Liquid laundry detergent + 0.8% encapsulated perfume according to the invention Area | Liquid fabric enhancer + 0.8% perfume according to the invention Area | Liquid fabric enhancer + 0.8% encapsulated perfume according to the invention Area |
|---|---|---|---|---|
| Ethyl_2_methyl_butyrate | 748 | 6617 | 10373 | 1523333 |
| Limonene | 5824798 | 39382532 | 6569387 | 7051555 |
| Melonal | 694956 | 2218584 | 85340 | 3171848 |
| Dihydromyrcenol | 25510835 | 114306456 | 35819699 | 29763083 |
| Ligustral | 2213984 | 6648864 | 1324661 | 2662205 |
| Tetrahydrolinalool | 59876421 | 245565429 | 57865250 | 35846824 |
| Methyl_phenyl_carbinyl_acetate | 2180484 | 6757126 | 5107641 | 11332823 |
| Koavone | 3110943 | 6232401 | 2515558 | 1273654 |
| Verdox | 35883188 | 39534099 | 28359962 | 8958762 |
| Vertenex | 14453069 | 17838622 | 15063834 | 3559771 |
| Diphenyloxide | 4620009 | 18733572 | 4880234 | 3403554 |
| Allyl_cyclohexane_propionate | 5059296 | 10167004 | 5600874 | 1406543 |
| Florhydral | 2586491 | 2843862 | 2398279 | 751176 |
| Flor_acetate | 51025417 | 155361150 | 48015625 | 17314960 |
| Floralozone | 24699776 | 20033009 | 24161774 | 5252890 |
| Pinyl_isobutyrate | 22743450 | 11908615 | 25539423 | 3840682 |
| Neobutenone | 1472503 | 2508259 | 1517013 | 462236 |
| Beta-ionone | 16039602 | 16182094 | 15501376 | 3683036 |
| Fructalate | 361850 | 2824506 | 759860 | 519923 |
| Sum | 278357822 | 719052802 | 281096162 | 141778859 |

Headspace Data—Olfactive Data for Perfume Microcapsules Comprising Melamine Formaldehyde Based Shells
Perfume Raw Materials Release in Headspace from Dry Fabrics

| Component name | Liquid laundry detergent + 0.8% perfume according to the invention Area | Liquid laundry detergent + 0.8% encapsulated perfume according to the invention Area | Liquid fabric enhancer + 0.8% perfume according to the invention Area | Liquid fabric enhancer + 0.8% encapsulated perfume according to the invention Area |
|---|---|---|---|---|
| Ethyl_2_methyl_butyrate | 269 | 1760 | 337 | 456778 |
| Limonene | 133109 | 51843445 | 221298 | 16715278 |
| Melonal | 105775 | 1000603 | 28601 | 1568156 |
| Dihydromyrcenol | 1451793 | 16809893 | 1446299 | 19053054 |
| Ligustral | 177326 | 1640004 | 94198 | 1933789 |
| Tetrahydrolinalool | 2714323 | 105434911 | 2969175 | 40901311 |
| Methyl_phenyl_carbinyl_acetate | 55771 | 362095 | 57722 | 3511910 |
| Koavone | 41685 | 10817150 | 67337 | 2409988 |
| Verdox | 777734 | 89313677 | 958577 | 18150667 |
| Vertenex | 514849 | 17483800 | 524435 | 3951354 |
| Diphenyloxide | 206900 | 2778046 | 237474 | 1484007 |
| Allyl_cyclohexane_propionate | 19597 | 4610843 | 49484 | 1094178 |
| Florhydral | 155099 | 1906963 | 120098 | 626995 |
| Flor_acetate | 644372 | 50290238 | 794809 | 16146296 |
| Floralozone | 425087 | 15687042 | 373396 | 5350502 |
| Pinyl_isobutyrate | 225804 | 13910361 | 218946 | 4481003 |
| Neobutenone | 10883 | 1398271 | 19380 | 318265 |
| Beta-ionone | 143142 | 10792666 | 183710 | 2772237 |
| Fructalate | 31697 | 791528 | 70428 | 310822 |
| Sum | 7835214 | 396873296 | 8435706 | 141236591 |

Headspace Data Olfactive Data for Perfume Microcapsules Comprising Polyacrylate Based Shells
Headspace Data—Perfume Raw Materials Release in Headspace from Damp Fabrics

|  | Sample Description | | | |
| --- | --- | --- | --- | --- |
| Component Name | Liquid laundry detergent + 0.8% perfume according to the invention Area | Liquid laundry detergent + 0.8% encapsulated perfume according to the invention Area | Liquid fabric enhancer + 0.8% perfume according to the invention Area | Liquid fabric enhancer + 0.8% encapsulated perfume according to the invention Area |
| Ethyl_2_Methyl_Butyrate | 482 | 531003 | 811 | 462773 |
| Limonene | 12489581 | 16216597 | 2370248 | 14294806 |
| Melonal | 888946 | 1689573 | 107836 | 1689055 |
| Dihydromyrcenol | 24904852 | 39102301 | 18272713 | 46040662 |
| Ligustral | 2044628 | 3761205 | 671664 | 3197217 |
| Tetrahydrolinalool | 66560928 | 72611425 | 26031177 | 84201862 |
| Methyl_Phenyl_Carbinyl_Acetate | 2648653 | 10335831 | 2779786 | 10888316 |
| Koavone | 3618159 | 3433602 | 1234755 | 3893902 |
| Verdox | 51224897 | 31045074 | 14433170 | 30009922 |
| Vertenex | 19597105 | 12359547 | 8631215 | 12049403 |
| Diphenyloxide | 6285844 | 8212190 | 3351834 | 6840400 |
| Allyl_Cyclohexane_Propionate | 5636273 | 3888821 | 3296331 | 3918361 |
| Florhydral | 3455954 | 2696022 | 1748605 | 2178402 |
| Flor_Acetate | 60729120 | 52855931 | 28367420 | 49635077 |
| Floralozone | 4570515 | 3251715 | 2225229 | 3145317 |
| Pinyl_Isobutyrate | 30947183 | 15507120 | 17204656 | 12507458 |
| Neobutenone | 1475751 | 1082599 | 791712 | 1095628 |
| Beta-Ionone | 17444427 | 13020759 | 9400387 | 12127064 |
| Fructalate | 228032 | 575389 | 425408 | 804562 |
| Sum | 314751329 | 292176705 | 141344956 | 298980186 |

Headspace Data—Headspace Data Olfactive Data for Perfume Microcapsules Comprising Polyacrylate Based Shells Perfume Raw Materials Release in Headspace from Dry Fabrics

| Component name | Liquid laundry detergent + 0.8% perfume according to the invention Area | Liquid laundry detergent + 0.8% encapsulated perfume according to the invention Area | Liquid fabric enhancer + 0.8% perfume according to the invention Area | Liquid fabric enhancer + 0.8% encapsulated perfume according to the invention Area |
| --- | --- | --- | --- | --- |
| Ethyl_2_methyl_butyrate | 538 | 760278 | 385 | 663423 |
| Limonene | 207655 | 34561856 | 136978 | 31850106 |
| Melonal | 75033 | 2637327 | 35460 | 2561718 |
| Dihydromyrcenol | 2081283 | 41807348 | 1512364 | 50043016 |
| Ligustral | 157410 | 7370782 | 60709 | 5544972 |
| Tetrahydrolinalool | 7476024 | 96304292 | 4950453 | 115865656 |
| Methyl_phenyl_carbinyl_acetate | 57739 | 10874526 | 49675 | 10514552 |
| Koavone | 52124 | 5365961 | 117542 | 5584865 |
| Verdox | 2481287 | 44866965 | 1798309 | 44391899 |
| Vertenex | 1210576 | 9924990 | 882641 | 10350976 |
| Diphenyloxide | 945955 | 5000551 | 802898 | 4108949 |
| Allyl_cyclohexane_propionate | 30761 | 2373616 | 28764 | 2579247 |
| Florhydral | 199633 | 1561218 | 159995 | 1887739 |
| Flor_acetate | 698595 | 38490017 | 628958 | 38964271 |
| Floralozone | 109994 | 2285181 | 92048 | 2354402 |
| Pinyl_isobutyrate | 225624 | 9681535 | 182716 | 10394561 |
| Neobutenone | 38304 | 710866 | 32980 | 837504 |
| Beta-ionone | 319894 | 5955643 | 307699 | 7133097 |
| Fructalate | 29670 | 569301 | 53665 | 822558 |
| Sum | 16398098 | 321102253 | 11834240 | 346453511 |

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A perfume comprising:
a.) form 0.0167% to 0.15% (Z)-non-6-en-1-ol;
b.) from 0.02% to 0.18% 1-methyl-2-[(1,2,2-trimethylbicyclo[3.1.0]hex-3-yl)methyl]-cyclopropanemethanol;
c.) from 0.003% to 0.03% (2E,6Z)-nona-2,6-dienal;
d.) from 0.03% to 0.3% 3-Ethoxy-4-hydroxy-benzaldehyde;
e.) from 0.05% to 0.45% [2-[1-(3,3-dimethylcyclohexy)ethoxy]-2-methylpropyl]propanoate;
f.) from 0.06% to 0.6% 1,6-Octadien-3-ol, 3,7-dimethyl-, acid-isomerized;
g.) from 0.06% to 0.6% [(4Z)-1-Cyclooct-4-enyl] methyl carbonate;
h.) from 0.06% to 0.6% 4-(Octahydro-4,7-methano-5H-inden-5-ylidene)butanal;
i.) from 0.1% to 0.9% 3,3-Dimethyl-5-(2,2,3-trimethyl-3-cyclopenten-1-yl)-4-penten-2-ol;
j.) from 0.115% to 1% 1-(5,5-Dimethyl-1-cyclohexen-1-yl)-4-penten-1-one;
k.) from 0.115% to 1% (12E)-oxacyclohexadec-12-en-2-one;
l.) from 0.115% to 1% Decanal;
m.) from 0.166% to 1.5% Dodecanal;
n.) from 0.2% to 1.8% 1,1'-oxybis-benzene;
o.) from 0.23% to 2.1% 2,6-dimethyl-5-Heptenal;
p.) from 0.33% to 3% β-Methyl-3-(1-methylethyl)-benzenepropanal;
q.) from 0.7% to 6.6% Prop-2-enyl 3-cyclohexylpropanoate;
r.) from 0.67% to 6% 4-EThyl-α,α-dimethyl-benzenepropanal;
s.) from 0.8% to 7.2% 1-phenylethyl acetate;
t.) from 0.8% to 7.5% α,α,6,6-tetramethyl-bicyclo[3.1.1]hept-2-ene-2-propanal;
u.) from 1% to 9% Diethyl cyclohexane-1,4-dicarboxylate;
v.) from 1.17% to 10.5% 2,4-Dimethyl-3-Cyclohexene-1-carboxaldehyde;
w.) from 1.3% to 12% (3Z)-3,4,5,6,6-pentamethyl-3-Hepten-2-one;
x.) from 1.3% to 12% 2-[2-(4-methyl-3-cyclohexen-1-yl)propyl]cyclopentanone;
y.) from 1.3% to 12% (3-pentyloxan-4-yl) acetate;
z.) from 1.5% to 13.5% 4-(2,6,6-Trimethyl-1-cyclohexen-1-yl)-3-buten-2-one;
aa.) from 1.5% to 13.5% 3-oxo-2-pentyl-cyclopentaneacetic acid methyl ester;
bb.) from 1.66% to 15% 4-(1,1-Dimethylethyl)cyclohexyl acetate;
cc.) from 1.66% to 15% Ethyl 2-methylbutanoate;
dd.) from 2% to 18% Orange Terpenes;
ee.) from 2.16% to 20% 2,6-Dimethyl-7-octen-2-ol;
ff.) from 3.5% to 30% 3,7-dimethyl-3-octanol;
gg.) from 3% to 25% (2-tert-butylcyclohexyl) acetate; and
hh.) from 5% to 40% 3a,4,5,6,7,7a-hexahydro-4,7-methano-1H-inden-6-yl acetate,
with the proviso that the sum of said ingredients in said perfume equals 100%.

2. A perfume delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, said perfume delivery system comprising a perfume according to claim 1.

3. A Polymer Assisted Delivery (PAD) system according claim 2, wherein said Polymer Assisted Delivery (PAD) system comprises a Polymer Assisted Delivery (PAD) Reservoir system.

4. The Polymer Assisted Delivery (PAD) Reservoir system of claim 3 said Polymer Assisted Delivery (PAD) Reservoir system comprising a perfume delivery particle that comprises a shell material and a core material, said shell material encapsulating said core material, said core material comprising a perfume according to claim 1 and said shell comprising a material selected from the group consisting of polyethylenes; polyamides; polystyrenes; polyisoprenes; polycarbonates; polyesters; polyacrylates; aminoplasts; polyolefins; polysaccharides; gelatin; shellac; epoxy resins; vinyl polymers; water insoluble inorganics; silicone; and mixtures thereof.

5. The Polymer Assisted Delivery (PAD) Reservoir system of claim 4 wherein said shell comprises melamine formaldehyde and/or cross linked melamine formaldehyde.

6. The Polymer Assisted Delivery (PAD) Reservoir system of claim 4 wherein said shell is coated by a water-soluble cationic polymer selected from the group that consists of polysaccharides, cationically modified starch and cationically modified guar, polysiloxanes, dimethyldiallylammonium polyhalogenides, copolymers of dimethyldiallylammonium polychloride and vinyl pyrrolidone, acrylamides, imidazoles, imidazolinium halogenides and imidazolium halogenides and polyvinyl amine and its copolymers with N-vinyl formamide.

7. The Polymer Assisted Delivery (PAD) Reservoir system of claim 6 wherein: said coating that coats said shell, comprises a cationic polymer and an anionic polymer.

8. The Polymer Assisted Delivery (PAD) Reservoir system of claim 7 wherein said cationic polymer comprises hydroxyl ethyl cellulose; and said anionic polymer comprises carboxyl methyl cellulose.

9. The Polymer Assisted Delivery (PAD) Reservoir system of claim 4, wherein said perfume delivery particle is a perfume microcapsule.

10. A consumer product comprising a perfume according to any of claim 1 and or a perfume delivery system according to claim 2 and a cleaning and/or treatment ingredient.

11. A method of treating and/or cleaning a situs, said method comprising
a) optionally washing and/or rinsing said situs;
b) contacting said situs with a composition selected from a perfume according to any of claim 1, a perfume delivery system according to any of claim 2, and/or a consumer product according to claim 10; and
c) optionally washing and/or rinsing said situs.

12. A perfume according to claim 1, said perfume comprising:
a.) form 0.025% to 0.075% (Z)-non-6-en-1-ol;
b.) from 0.03% to 0.09% 1-methyl-2-[(1,2,2-trimethylbicyclo[3.1.0]hex-3-yl)methyl]-cyclopropanemethanol;

c.) from 0.005% to 0.015% (2E,6Z)-nona-2,6-dienal;
d.) from 0.050% to 0.15% 3-Ethoxy-4-hydroxy-benzaldehyde;
e.) from 0.075% to 0.225% [2-[1-(3,3-dimethylcyclohexy)ethoxy]-2-methylpropyl]propanoate;
f.) from 0.1% to 0.3% 1,6-Octadien-3-ol, 3,7-dimethyl-, acid-isomerized;
g.) from 0.1% to 0.3% [(4Z)-1-Cyclooct-4-enyl] methyl carbonate;
h.) from 0.1% to 0.3% 4-(Octahydro-4,7-methano-5H-inden-5-ylidene)butanal;
i.) from 0.15% to 0.45% 3,3-Dimethyl-5-(2,2,3-trimethyl-3-cyclopenten-1-yl)-4-penten-2-ol;
j.) from 0.175% to 0.525% 1-(5,5-Dimethyl-1-cyclohexen-1-yl)-4-penten-1-one;
k.) from 0.175% to 0.525% (12E)-oxacyclohexadec-12-en-2-one;
l.) from 0.175% to 0.6% Decanal;
m.) from 0.25% to 0.75% Dodecanal;
n.) from 0.3% to 0.9% 1,1'-oxybis-benzene;
o.) from 0.35% to 1.05% 2,6-dimethyl-5-Heptenal;
p.) from 0.5% to 1.5% β-Methyl-3-(1-methylethyl)-benzenepropanal;
q.) from 1.1% to 3.3% Prop-2-enyl 3-cyclohexylpropanoate;
r.) from 1% to 3% 4-EThyl-α,α-dimethyl-benzenepropanal;
s.) from 1.2% to 4% 1-phenylethyl acetate;
t.) from 1.25% to 4% α,α,6,6-tetramethyl-bicyclo[3.1.1]hept-2-ene-2-propanal;
u.) from 1.5% to 4.5% Diethyl cyclohexane-1,4-dicarboxylate;
v.) from 1.75% to 5% 2,4-Dimethyl-3-Cyclohexene-1-carboxaldehyde;
w.) from 2% to 6% (3Z)-3,4,5,6,6-pentamethyl-3-Hepten-2-one;
x.) from 2% to 6% 2-[2-(4-methyl-3-cyclohexen-1-yl)propyl]cyclopentanone;
y.) from 2% to 6% (3-pentyloxan-4-yl) acetate;
z.) from 2.25% to 6% 4-(2,6,6-Trimethyl-1-cyclohexen-1-yl)-3-buten-2-one;
aa.) from 2.25% to 6% 3-oxo-2-pentyl-cyclopentaneacetic acid methyl ester;
bb.) from 2.5% to 7.5% 4-(1,1-Dimethylethyl)cyclohexyl acetate;
cc.) from 2.5% to 7.5% Ethyl 2-methylbutanoate;
dd.) from 3% to 9% Orange Terpenes;
ee.) from 3% to 9% 2,6-Dimethyl-7-octen-2-ol;
ff.) from 5% to 16% 3,7-dimethyl-3-octanol;
gg.) from 4% to 14% (2-tert-butylcyclohexyl) acetate; and
hh.) from 8% to 25% 3a,4,5,6,7,7a-hexahydro-4,7-methano-1H-inden-6-yl acetate, with the proviso that the sum of said ingredients in said perfume equals 100%.

13. A perfume according to claim 1, said perfume comprising:
a.) form 0.03% to 0.06% (Z)-non-6-en-1-ol;
b.) from 0.05% to 0.07% 1-methyl-2-[(1,2,2-trimethylbicyclo[3.1.0]hex-3-yl)methyl]-cyclopropanemethanol;
c.) from 0.005% to 0.015% (2E,6Z)-nona-2,6-dienal;
d.) from 0.08% to 0.12% 3-Ethoxy-4-hydroxy-benzaldehyde;
e.) from 0.12% to 0.18% [2-[1-(3,3-dimethylcyclohexy)ethoxy]-2-methylpropyl]propanoate;
f.) from 0.15% to 0.25% 1,6-Octadien-3-ol, 3,7-dimethyl-, acid-isomerized;
g.) from 0.15% to 0.25% [(4Z)-1-Cyclooct-4-enyl] methyl carbonate;
h.) from 0.15% to 0.25% 4-(Octahydro-4,7-methano-5H-inden-5-ylidene)butanal;
i.) from 0.24% to 0.36% 3,3-Dimethyl-5-(2,2,3-trimethyl-3-cyclopenten-1-yl)-4-penten-2-ol;
j.) from 0.27% to 0.45% 1-(5,5-Dimethyl-1-cyclohexen-1-yl)-4-penten-1-one;
k.) from 0.28% to 0.45% (12E)-oxacyclohexadec-12-en-2-one;
l.) from 0.28% to 0.45% Decanal;
m.) from 0.4% to 0.6% Dodecanal;
n.) from 0.48% to 0.72% 1,1'-oxybis-benzene;
o.) from 0.56% to 0.85% 2,6-dimethyl-5-Heptenal;
p.) from 0.8% to 1.2% β-Methyl-3-(1-methylethyl)-benzenepropanal;
q.) from 1.76% to 2.64% Prop-2-enyl 3-cyclohexylpropanoate;
r.) from 1.6% to 2.4% 4-EThyl-α,α-dimethyl-benzenepropanal;
s.) from 1.9% to 2.9% 1-phenylethyl acetate;
t.) from 2% to 3% α,α,6,6-tetramethyl-bicyclo[3.1.1]hept-2-ene-2-propanal;
u.) from 2.4% to 3.6% Diethyl cyclohexane-1,4-dicarboxylate;
v.) from 2.8% to 4.2% 2,4-Dimethyl-3-Cyclohexene-1-carboxaldehyde;
w.) from 3.2% to 4.8% (3Z)-3,4,5,6,6-pentamethyl-3-Hepten-2-one;
x.) from 3.2% to 4.8% 2-[2-(4-methyl-3-cyclohexen-1-yl)propyl]cyclopentanone;
y.) from 3.2% to 4.8% (3-pentyloxan-4-yl) acetate;
z.) from 3.6% to 5.4% 4-(2,6,6-Trimethyl-1-cyclohexen-1-yl)-3-buten-2-one;
aa.) from 3.6% to 5.4% 3-oxo-2-pentyl-cyclopentaneacetic acid methyl ester;
bb.) from 4% to 6% 4-(1,1-Dimethylethyl)cyclohexyl acetate;
cc.) from 4% to 6% Ethyl 2-methylbutanoate;
dd.) from 4.8% to 7.5% Orange Terpenes;
ee.) from 5.2% to 7.8% 2,6-Dimethyl-7-octen-2-ol;
ff.) from 8% to 12% 3,7-dimethyl-3-octanol;
gg.) from 7.5% to 11% (2-tert-butylcyclohexyl) acetate; and
hh.) from 14% to 17% 3a,4,5,6,7,7a-hexahydro-4,7-methano-1H-inden-6-yl acetate, with the proviso that the sum of said ingredients in said perfume equals 100%.

* * * * *